(12) United States Patent
Chaves et al.

(10) Patent No.: US 7,368,584 B2
(45) Date of Patent: *May 6, 2008

(54) MERCAPTO-FUNCTIONAL SILANE

(75) Inventors: Antonio Chaves, Chappaqua, NY (US);
Eric R. Pohl, Mount Kisco, NY (US);
Christopher M. Hartshorn, Ossining, NY (US)

(73) Assignee: Momentive Performance Materials Inc., Wilton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/505,221

(22) Filed: Aug. 14, 2006

(65) Prior Publication Data

US 2008/0039645 A1 Feb. 14, 2008

(51) Int. Cl.
*C07F 7/02* (2006.01)
(52) U.S. Cl. .................................................. 556/400
(58) Field of Classification Search .................... None
See application file for complete search history.

(56) References Cited

U.S. PATENT DOCUMENTS

| | | | |
|---|---|---|---|
| 2,811,542 A | 10/1957 | Speier et al. | |
| 3,065,254 A | 11/1962 | Silva | |
| 3,445,496 A | 5/1969 | Ryan | |
| 3,661,954 A | 5/1972 | Legrow | |
| 3,692,812 A | 9/1972 | Berger | |
| 3,798,196 A | 3/1974 | Rocktaeschel et al. | |
| 3,869,340 A | 3/1975 | Kotzsch | |
| 3,922,340 A | 11/1975 | Miwa | |
| 3,922,436 A | 11/1975 | Bell et al. | |
| 3,956,353 A | 5/1976 | Plueddemann et al. | |
| 3,971,883 A | 7/1976 | Meeks et al. | |
| 4,060,539 A | 11/1977 | Seiler et al. | |
| 4,152,347 A | 5/1979 | Pletka et al. | |
| 4,574,133 A | 3/1986 | Umpleby | |
| 4,820,751 A | 4/1989 | Takeshita | |
| 5,116,886 A | 5/1992 | Wolff et al. | |
| 5,326,895 A | 7/1994 | Kubota et al. | |
| 5,663,226 A | 9/1997 | Scholl | |
| 6,005,027 A | 12/1999 | Guillet et al. | |
| 6,127,468 A | 10/2000 | Cruse | |
| 6,204,339 B1 | 3/2001 | Waldman | |
| 6,359,046 B1 | 3/2002 | Cruse | |
| 6,414,061 B1 | 7/2002 | Cruse | |
| 6,528,673 B2 | 3/2003 | Cruse | |
| 6,548,594 B2 | 4/2003 | Lunginsland et al. | |
| 6,608,125 B2 | 8/2003 | Cruse | |
| 6,635,700 B2 | 10/2003 | Cruse et al. | |
| 6,683,135 B2 | 1/2004 | Cruse | |
| 6,777,569 B1 | 8/2004 | Westmeyer | |
| 6,849,754 B2 | 2/2005 | Deschler et al. | |
| 7,074,876 B2 | 7/2006 | Cruse | |
| 7,078,551 B2 | 7/2006 | Cruse | |
| 7,081,500 B2 | 7/2006 | Cruse | |
| 7,122,590 B2 | 10/2006 | Cruse | |
| 2001/0009966 A1 | 7/2001 | Wunsch | |
| 2002/0016487 A1 | 2/2002 | Kayser et al. | |
| 2003/0130388 A1 | 7/2003 | Luginsland | |
| 2003/0199619 A1 | 10/2003 | Cruse | |
| 2004/0014840 A1 | 1/2004 | Hong et al. | |
| 2005/0009955 A1 | 1/2005 | Cohen et al. | |
| 2005/0245753 A1 | 11/2005 | Cruse | |
| 2005/0245754 A1 | 11/2005 | Glatzer | |
| 2006/0025506 A1 | 2/2006 | Weller | |
| 2006/0036034 A1 | 2/2006 | Chaves et al. | |
| 2006/0041063 A1 | 2/2006 | Cruse et al. | |
| 2006/0183831 A1 | 8/2006 | Hsu et al. | |
| 2006/0183866 A1 | 8/2006 | Pohl | |
| 2006/0217474 A1 | 9/2006 | Cruse et al. | |
| 2006/0217475 A1 | 9/2006 | Cruse et al. | |
| 2006/0281841 A1 | 12/2006 | Weller | |
| 2007/0083011 A1 | 4/2007 | Pohl | |
| 2007/0197725 A1 | 8/2007 | Chaves | |
| 2007/0197812 A1 | 8/2007 | Chaves | |
| 2007/0197813 A1 | 8/2007 | Chaves | |
| 2007/0228322 A1 | 10/2007 | Chaves | |

FOREIGN PATENT DOCUMENTS

| | | |
|---|---|---|
| AU | 730753 | 7/1997 |
| DE | 2050467 | 5/1971 |
| DE | 10163945 | 12/2001 |
| EP | 0097516 | 1/1984 |
| EP | 0 396 364 | 11/1990 |
| EP | 0631982 | 1/1995 |

(Continued)

OTHER PUBLICATIONS

U.S. Appl. No. 10/922,426, filed Aug. 2004, Cruse et al.

(Continued)

*Primary Examiner*—Shaojia Anna Jiang
*Assistant Examiner*—MLouisa Lao
(74) *Attorney, Agent, or Firm*—Dominick G. Vicari

(57) ABSTRACT

The disclosure herein relates to organofunctional silanes and mixtures of organofunctional silanes possessing mercaptan and hydrocarbyl and/or heterocarbyl functionality. These silanes reduce or eliminate the generation of volatile organic compounds (VOC's) during use, aid in the processing of filled elastomeric materials and enhance the end-use properties of the filled elastomer. The present disclosure relates to the composition of these silanes.

23 Claims, No Drawings

FOREIGN PATENT DOCUMENTS

| | | |
|---|---|---|
| EP | 0784072 | 7/1997 |
| FR | 2 382 456 | 9/1978 |
| JP | 58176538 | 10/1983 |
| JP | H07258474 | 10/1995 |
| WO | WO99/09036 | 2/1999 |
| WO | WO99/20682 | 4/1999 |
| WO | 03/091314 | 11/2003 |
| WO | WO2004/005395 | 1/2004 |
| WO | WO2005/007660 | 1/2005 |
| WO | WO2005/040272 | 5/2005 |

OTHER PUBLICATIONS

U.S. Appl. No. 11/208,367, filed Aug. 2005, Cruse et al.
U.S. Appl. No. 11/358,550, filed Feb. 2006, Chaves et al.
U.S. Appl. No. 11/358,818, filed Feb. 2006, Chaves et al.
U.S. Appl. No. 11/358,369, filed Feb. 2006, Chaves et al.
U.S. Appl. No. 11/358,861, filed Feb. 2006, Chaves et al.
U.S. Appl. No. 11/104,103, filed Apr. 2005, Chaves et al.
"The Siloxane Bond, Physical Properties and Chemical Transformations", M.G. Voronkov, V.P. Mileshkevich and Yu. A. Yuzhelevskii, Consultant Bureau, a Division of Plenum Publishing Company, New York (1978), Chapter 5.
U.S. Appl. No. 11/505,166, filed Aug. 2006, Chaves et al.
U.S. Appl. No. 11/505,055, filed Aug. 2006, Chaves et al.
U.S. Appl. No. 11/505,178, filed Aug. 2006, Chaves et al.
GE Advanced Materials Silicones "Low VOC Silanes for Silica Tire", Feb. 22, 2005.
Bonsignore P.V. et al., (1960) APolyalkylene disulfides and polysulfides containing silicon@, *Journal of Organic Chemstry* 25 pp. 237-240.

Takiguchi T. et al. (1983) Some Fundamental Investigations Viewed in Industrial Aspects on the Synthesis of Organosilicon Monomers and Polymers with Some Novel Properties and Functions@, *AGKGAA* 43 pp. 75-82.
Dvorak, M. et al. (1977) ACarbonfunctional organosilicon compounds substituted in the .alpha-position. II. Phosphorus-containing organosilicon compounds substituted in the .alpha.-position. II. Phosphorus-containing organosilicon compounds@. *Chemicky Prumysl*, 27(5), pp. 9-2789.
Andrianov, K.A. et al. (1962) AReaction of replacement of chlorine in .alpha.-chloromethylmethylalkoxysilanes by residues of diethyl of dibutyl dithiophosphoric or diphenyldithiophosphinic acids@., *Izvestiya Akademii Nauk SSSR*, pp. 2-3353.
Prashant G. Joshi, GE Advanced Materials—Silicones, "Low Voc Silanes for Silica Tires", 2005.
U.S. Appl. No. 10/918,828, filed Aug. 2004, Weller.
U.S. Appl. No. 10/903,960, filed Jul. 2004, Weller.
Teng, Zhu et al.; "Palladium-induced intramolecular coupling reactions of some alkenyl (2-iodobenzyl)silanes" Helvetica Chimica Acta, 82,(4), 515-521, Coden:HCACAV;ISSN: 0018-019X, 1999, XP002372297.
U.S. Appl. No. 10/128,804, filed Aug. 2005, Cruse.
U.S. Appl. No. 11/398,125, filed Apr. 2006, Cruse.
U.S. Appl. No. 11/398,132, filed Apr. 2006, Pohl.
Joshi PG: "Low Voc Silanes for Silica Tires"; Spring Technical Meeting-American Chemical Society, Rubber Division, 167th San Antonio, Texas USA, May 16-18, 2005, pp. 47/1-47/9, XP009072692, ISSN: 1547-1969.

MERCAPTO-FUNCTIONAL SILANE

FIELD OF THE INVENTION

The present disclosure relates to organofunctional silanes and also relates to mixtures of organofunctional silanes. The disclosure relates to a composition of these silanes.

DESCRIPTION OF THE RELATED ART

Mercaptosilanes and their use as coupling agents in filled elatomers are known in the art. However, these silanes are very reactive with the fillers and organic polymers and are difficult to use in preparing filled elastomers. When these silanes are used at levels necessary to achieve optimum coupling of the filler to the polymer, the uncured filled elastomer has short scorch times and poorly dispersed fillers. Long scorch times are necessary for mixing of the filler and other ingredients with the polymer, extrusion of the uncured elastomer and fabrication of articles without premature crosslinking or formation of high viscosity compounds. Good dispersion of the filler is required to achieve end-use properties, such as weatherability, wear, tear-resistance and so on. These silanes are also derived from monol functional alcohols that generate volatile organic compound (VOC) emissions during fabrication and use.

Glycol derivatives of organosilanes are known in the art. However, these silane derivatives suffer from a tendency to yield bridged structures in favor of cyclic structures exclusively or primarily, leading to high viscosities and gellation, which limits their usefulness in elastomer manufacture.

In addition to the need to reduce VOC's during the preparation of inorganic filled elastomers, there is also a need to improve the dispersion of the inorganic fillers in organic polymers while maintaining processability of the elastomeric compositions. Better dispersion improves the performance of cured articles, such as tires, by reducing rolling resistance, heat build-up and wear.

Recently, the present inventors addressed in U.S. patent application Ser. Nos. 11/358,550; 11/358,818; 11/358,369; 11/358,861 all filed on Feb. 21, 2006, the scorch, VOC emissions and coupling performance of filled elastomers using organofunctional silanes or mixtures of organofunctionals silanes that contain both blocked and free mercaptan groups. In addition, the present inventors addressed in U.S. patent application Ser. No. 11/104,103, filed on Apr. 12, 2005, the VOC emissions using organofunctional silanes containing dialkoxysilyl groups.

SUMMARY OF THE INVENTION

In one embodiment, the present disclosure is directed to a mercaptofunctional silane composition comprising at least one organofunctional silane selected from the group consisting of:

(i) mercaptosilane possessing at least one hydroxyalkoxysilyl group and/or a cyclic dialkoxysilyl group, (ii) hydrocarbylsilane or heterocarbylsilane possessing at least one hydroxyalkoxysilyl group and/or a cyclic dialkoxysilyl group, (iii) mercaptosilane dimer in which the silicon atoms of the mercaptosilane units are bonded to each other through a bridging dialkoxy group, each silane unit optionally possessing at least one hydroxyalkoxysilyl group and/or a cyclic dialkoxysilyl group, (iv) hydrocarbylsilane and/or heterocarbylsilane dimer in which the silicon atoms of the hydrocarbylsilane and/or heterocarbylsilane units are bonded to each other through a bridging dialkoxy group, each silane unit optionally possessing at least one hydroxyalkoxysilyl group and/or a cyclic dialkoxysilyl group, (v) silane dimer possessing a mercaptosilane unit, the silicon atom of which is bonded to the silicon atom of a hydrocarbylsilane and/or heterocarbylsilane unit through a bridging dialkoxy group, each silane unit optionally possessing at least one hydroxyalkoxysilyl group and/or a cyclic dialkoxysilyl group, (vi) mercaptosilane oligomer in which the silicon atoms of adjacent mercaptosilane units are bonded to each other through a bridging dialkoxy group, the terminal mercaptosilane units possessing at least one hydroxyalkoxysilyl group and/or a cyclic dialkoxysilyl group, (vii) hydrocarbylsilane and/or heterocarbylsilane oligomer in which the silicon atoms of adjacent hydrocarbylsilane and/or heterocarbylsilane units are bonded to each other through a bridging dialkoxy group, the terminal hydrocarbylsilane and/or heterocarbylsilane units possessing at least one hydroxyalkoxysilyl group and/or a cyclic dialkoxysilyl group, and (viii) silane oligomer possessing at least one mercaptosilane unit and at least one hydrocarbylsilane and/or heterocarbylsilane unit, the silicon atoms of adjacent silane units being bonded to each other through a bridging dialkoxy group, the terminal silane units possessing at least one hydroxyalkoxysilyl group and/or a cyclic dialkoxysilyl group, with the provisio that, where the composition contains one or more of (i), (iii) and (vi), the composition additionally contains one or more of (ii), (iv), (v), (vii) and (viii), and where the composition contains one or more of (ii), (iv) and (vii), the composition additionally contains one or more of (i), (iii), (v), (vi) and (viii).

In one other embodiment as will be appreciated from the foregoing, compositions made by the process described herein can include one or more silane dimers and/or oligomers in which adjacent silane units are bonded to each other through bridged dialkoxysilane structures derived from polyhydroxy-containing compounds, e.g., diols (glycols), triols, tetrols, etc., all of which are low volatile organic compounds (VOCs) relative to simple monohydroxy-containing compounds such as methanol and ethanol which are released by known organosilanes.

In another embodiment, it will also be appreciated that all of the compositions made by the process within the scope of the invention contain both mercapto, and hydrocarbyl and/or heterocarbyl functionalities, either present in the same silane or in mixtures of individual silanes. While it is known that silanes possessing exclusively mercaptan functionality are prone to scorch, it has come as a surprise that the compositions of this invention which possess both mercaptan, and hydrocarbyl and/or heterocarbyl functionalities, possess long scorch times, e.g., approaching those of silanes possessing exclusively blocked mercaptan or polysulfide groups, but with significantly better performance than the latter.

DETAILED DESCRIPTION OF THE INVENTION

The expression "organofunctional silane" as used herein shall be understood to mean a non-polymeric, dimeric or oligomeric silane possessing mercaptan and hydrocarbyl and/or heterocarbyl functionality and at least one hydroxyalkoxysilyl and/or cyclic dialkoxysilyl group, and, in the case of the dimeric and oligomeric organofunctional silanes, possessing dialkoxy bridging groups linking adjacent silane units.

In one embodiment herein, it will be understood that all ranges herein include all subranges therebetween. In another specific embodiment herein, it will be understood that all listings of members of a group can further comprise combinations of any two or more of the members of said group. In another embodiment herein, it will be understood that U.S. patent applications, with the same inventors as herein, and filed on same date as the subject application, and entitled: Process of Making Mercapto-functional Silane; A Free Flowing Filler Composition Comprising Mercapto-functional Silane; and A Rubber Composition and Articles Both Comprising Mercapto-functional Silane are all incorporated by reference herein in their entireties.

In another embodiment herein there is provided a process for the preparation of a mercaptofunctional silane comprising:

a) reacting at least one organofunctional silane selected from the group consisting of:

$$G^1\text{---}(SiX_3)_s \tag{1}$$

$$[G^3\text{---}(YG^2\text{---})_kY]_j\text{---}G^2\text{---}(SiX_3)_s \tag{2}$$

and at least one mercapto functional silane of general formula:

$$(HS)_r\text{---}G^2\text{---}(SiX_3)_s \tag{3}$$

wherein:

each occurrence of Y is independently selected from a polyvalent species $(\text{---}Q)_a[C(\text{==}E)]_b(A\text{---})_c$, wherein the atom (E) is attached to an unsaturated carbon atom; each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of $G^3$ is independently selected from the group consisting of monovalent and polyvalent groups derived by substitution of alkyl, alkenyl, aryl, or aralkyl wherein $G^3$ can have from 1 to about 30 carbon atoms, with the proviso that if $G^3$ is monovalent, $G^3$ can be hydrogen;

each occurrence of X is independently selected from the group consisting of ---Cl, ---Br, RO---, RC(==O)O---, $R_2C$==NO---, $R_2NO$---, $R_2N$---, ---R, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms; each occurrence of Q is independently selected from the group consisting of oxygen, sulfur, and (---NR---) and with the proviso that when Q is sulfur, b is 0;

each occurrence of A is independently selected from the group consisting of oxygen, sulfur, and (---NR---) and with the proviso that when A is sulfur, b is 0;

each occurrence of E is independently selected from the group consisting of oxygen, sulfur, and (---NR---);

each occurrence of the subscripts, a, b, c, j, k, r, and s are independently integers given by a is 0 or 1; b is 0 or 1; c is 0 or 1; j is of from about 1 to about 3; k is of from about 0 to about 15; r is of from about 1 to about 3; and s is of from about 1 to about 3, and with the proviso that each of the above structures (1), (2) and (3) contains at least one hydrolysable X group;

b) with one or more polyhydroxy-containing compounds of the general formula:

$$G^4(OH)_d \tag{6}$$

wherein $G^4$ is a hydrocarbon group of from 1 to about 15 carbon atoms or a heterocarbyl group of from 4 to about 15 carbon atoms containing one or more etheric oxygen atoms and d is an integer of from about 2 to about 8, under tranesterification reaction conditions.

In one embodiment herein, organofunctional silanes (i)-(viii) described herein, and their mixtures, can be obtained, inter alia, from one or more silane reactants of the general formulae:

$$G^1\text{---}(SiX_3)_s \tag{1}$$

$$[G^3\text{---}(YG^2\text{---})_kY]_j\text{---}G^2\text{---}(SiX_3)_s \tag{2}$$

$$(HS)_r\text{---}G^2\text{---}(SiX_3)_s \tag{3}$$

wherein:

each occurrence of Y is independently selected from a polyvalent species $(\text{---}Q)_a[C(\text{==}E)]_b(A\text{---})_c$, wherein the atom (E) is attached to an unsaturated carbon atom;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of $G^3$ is independently selected from the group consisting of monovalent and polyvalent groups derived by substitution of alkyl, alkenyl, aryl, or aralkyl wherein $G^3$ can have from 1 to about 30 carbon atoms, with the proviso that if $G^3$ is monovalent, $G^3$ can be hydrogen;

each occurrence of X is independently selected from the group consisting of ---Cl, ---Br, RO---, RC(==O)O---, $R_2C$==NO---, $R_2NO$---, $R_2N$---, ---R, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms;

each occurrence of Q is independently selected from the group consisting of oxygen, sulfur, and (---NR---) and with the proviso that when Q is sulfur, b is 0;

each occurrence of A is independently selected from the group consisting of oxygen, sulfur, and (---NR---) and with the proviso that when A is sulfur, b is 0;

each occurrence of E is independently selected from the group consisting of oxygen, sulfur, and (---NR---);

each occurrence of the subscripts, a, b, c, j, k, r, and s are independently integers given by a is 0 or 1 and more specifically 1; b is 0 or 1 and more specifically 0; c is 0 or 1 and more specifically 0; j is specifically of from about 1 to about 3, more specifically from about 1 to about 2 and most specifically 1; k is specifically of from about 0 to about 15, more specifically from about 0 to about 5, and most specifically from about 0 to about 2; r is specifically of from about 1 to about 3, and more specifically about 1; and s is specifically of from about 1 to about 3, and more specifically about 1, and with the proviso that each of the above structures (1), (2) and (3) contains at least one hydrolysable X group.

In one particular embodiment of the invention, the silane reactants are trialkoxysilanes represented by at least one of the general Formulae (4) and (5):

$$(RO)_3SiG^1 \quad (4)$$

$$(RO)_3SiG^2SH \quad (5)$$

wherein each R independently has one of the aforestated meanings and, advantageously, is a methyl, ethyl, propyl, isopropyl, n-butyl, or sec-butyl group; $G^2$ is an alkylene group of from 1 to about 12 carbon atoms; and, $G^1$ is an alkyl group of from 3 to about 18 carbon atoms.

In a specific embodiment herein, mixtures of silane monomers ((1), (2) and/or (3)) can be used, such as the non-limiting examples of, two or more mercaptotrialkoxysilanes of Formula (5), two or more hydrocarbyltrialkoxysilanes of Formula (4) and mixtures of one or more mercaptotrialkoxysilanes of Formula (5) and one or more hydrocarbyltrialkoxysilanes of Formula (4) with R, $G^1$ and $G^2$ in these silanes being defined as in silanes of Formulae (1) and (3).

In one embodiment herein, in a silane dimer or oligomer, each silane unit of the dimer or oligomer is bonded to an adjacent silane unit through a bridging group resulting from the reaction of the selected silane monomer(s) with one or more polyhydroxy-containing compounds of the general formula:

$$G^4(OH)_d \quad (6)$$

wherein $G^4$ is a hydrocarbon group of from 1 to about 15 carbon atoms or a heterocarbyl group of from 4 to about 15 carbon atoms containing one or more etheric oxygen atoms and d is an integer of specifically from about 2 to about 8, more specifically of from about 2 to about 4 and most specifically about 2.

In one embodiment herein, polyhydroxy-containing compound of Formula (6) is a diol (glycol) of at least one of the general Formulae (7) and (8):

$$HO(R^0CR^0)_fOH \quad (7)$$

$$HO(CR^0_2CR^0_2O)_eH \quad (8)$$

wherein $R^0$ is independently given by one of the members listed above for R, f is 2 to about 15 and e is 2 to about 7. In one embodiment, some representative non-limiting examples of such diols are $HOCH_2CH_2OH$, $HOCH_2CH_2CH_2OH$, $HOCH_2CH_2CH_2CH_2OH$, $HOCH_2CH(CH_3)CH_2OH$, $(CH_3)_2C(OH)CH_2CH(OH)CH_3$, $CH_3CH(OH)CH_2CH_2OH$, a diol possessing an etheric oxygen-containing group such as $HOCH_2CH_2OCH_2CH_2OH$, $HOCH_2CH_2CH_2OCH_2CH_2CH_2OH$, $HOCH_2CH(CH_3)OCH_2CH(CH_3)OH$ and a diol possessing a polyether backbone such as the non-limiting example of $HOCH_2CH_2OCH_2CH_2OCH_2CH_2OH$, a diol of Formula (8) in which $R^0$ is hydrogen or methyl and e is 3 to about 7.

In another embodiment herein, the polyhydroxy-containing compound of Formula (6) is a diol of Formula (7).

In another embodiment herein, polyhydroxy-containing compound of Formula (6) possesses higher hydroxyl functionality, and is such as the non-limiting examples selected from the group consisting of, a triol or tetrol, of the general Formula (9):

$$G^4(OH)_d \quad (9)$$

wherein $G^4$ is a is a substituted hydrocarbon group from 2 to about 15 carbon atoms or a substituted heterocarbon from 4 to about 15 carbon atoms and contains one or more etheric oxygen atoms; and d is an integer of from 3 to about 8. In one embodiment some non-limiting examples of higher hydroxyl functionality compounds (9) include glycerol, trimethylolethane, trimethylolpropane, 1,2,4-butanetriol, 1,2,6-hexanetriol, pentaerythritol, dipentaerythritol, tripentaerythritol, mannitol, galacticol, sorbitol, and combinations thereof.

In another embodiment, mixtures of polyhydroxy-containing compounds of Formula (6) can also be used herein.

In one embodiment herein, organofunctional silanes (i)-(viii) and mixtures thereof can be prepared by the process which comprises reacting at least one silane of one or more of general Formulae (1), (2), and/or (3):

$$G^1\text{—}(SiX_3)_3 \quad (1)$$

$$[G^3\text{—}(YG^2\text{—})_kY]_j\text{—}G^2\text{—}(SiX_3)_s \quad (2)$$

$$(HS)_r\text{—}G^2\text{—}(SiX_3)_s \quad (3)$$

with at least one polyhydroxy-containing compound of the general Formula (6):

$$G^4(OH)_d \quad (6)$$

wherein each occurrence of $G^1$, $G^2$, $G^3$, $G^4$, R, Y, X, a, b, c, d, j, k, r, and s are defined as herein, and with the proviso that at least one of the X is a hydrolyzable group, each of the aforesaid having the meanings previously stated, under transesterification reaction conditions.

In a first embodiment of the foregoing process, at least one hydrocarbyl of Formula (1) and/or heterocarbylsilane of Formula (2) is transesterified with at least one polyhydroxy-containing compound of Formula (6), optionally, in the presences of catalyst, e.g., transesterification catalyst, to provide one or more organofunctional hydrocarbylsilane and/or heterocarbylsilanes (ii), (iv) and (vii), and mercaptosilane of Formula (3) is transesterified with at least one polyhydroxy-containing compound of Formula (6), optionally, in the presences of catalyst, e.g., transesterification catalyst, to provide one or more part or all of the mercaptosilane(s) providing one or more organofunctional silanes (i), (iii), and (vi), any of which can be in admixture with one or more of (ii), (iv), and (vii).

In a second embodiment of the foregoing process, organofunctional silanes (i), (iii) and (vi) can further transesterify with organofunctional silanes (ii), (iv) and (vii) to form (v) or (viii), any of which can be in admixture with one or more of (i), (ii), (iii), (iv), (vi) and (vii). In one embodiment the mercaptofunctional silane composition described herein comprises at least one mixture selected from the group consisting of (i) and one or more of (ii), (iv), (v), (vii) and (viii); (ii) and one or more of (iii), (v), (vi) and (viii); (iii) and one or more of (v), (vii) and (viii); (iv) and one or more of (v), (vi) and (viii); (v) and either or both of (vi) and (vii); (vi) and either or both of (vii) and (viii); and, (vii) and (viii). In another embodiment there is provided a mercaptofunctional silane composition as described herein wherein (i) possesses one or two hydroxyalkoxysilyl groups and/or a cyclic dialkoxysilyl group; (ii) possesses one or two hydroxyalkoxysilyl groups and/or a cyclic dialkoxysilyl group; each silane unit of (iii) independently possesses one or two hydroxyalkoxysilyl groups and/or a cyclic dialkoxysilyl group; each silane unit of (iv) independently possesses one or two hydroxyalkoxysilyl groups and/or a cyclic dialkoxysilyl group; each silane unit of (v) independently possesses one or two hydroxyalkoxysilyl groups and/or a cyclic dialkoxysilyl group; (vi) possesses from 3 to about 20 mercaptosilane units, the terminal mercaptosilane units independently possessing one or two hydroxyalkoxysilyl groups and/or a cyclic dialkoxysilyl group; (vii) possesses from 3 to about 20 hydrocarbylsilane and/or heterocarbylsilane units, the terminal hydrocarbylsilane or heterocarbylsilane units independently possessing one or two hydroxyalkoxysilyl groups and/or a cyclic dialkoxysilyl group; and, (viii) possesses from 3 to about 40 silane units of which from 1 to about 20 are mercaptosilane units and from 1 to about 20 are hydrocarbylsilane and/or heterocarbylsilane units, the terminal silane units independently possessing one or two hydroxyalkoxysilyl groups and/or a cyclic dialkoxysilyl group. In yet another embodiment there is provided a mercaptofunctional silane composition as described herein wherein (i) possesses one or two hydroxyalkoxysilyl groups and/or a cyclic dialkoxysilyl group; (ii) possesses one or two hydroxyalkoxysilyl groups and/or a cyclic dialkoxysilyl group; each silane unit of (iii) independently possesses one or two hydroxyalkoxysilyl groups and/or a cyclic dialkoxysilyl group; each silane unit of (iv) independently possesses one or two hydroxyalkoxysilyl groups and/or a cyclic dialkoxysilyl group; each silane unit of (v) independently possesses one or two hydroxyalkoxysilyl groups and/or a cyclic dialkoxysilyl group; (vi) possesses from 3 to about 10 mercaptosilane units, the terminal mercaptosilane units independently possessing one or two hydroxyalkoxysilyl groups and/or a cyclic dialkoxysilyl group; (vii) possesses from 3 to about 10 hydrocarbylsilane and/or heterocarbylsilane units, the terminal hydrocarbylsilane or heterocarbylsilane units independently possessing one or two hydroxyalkoxysilyl groups and/or a cyclic dialkoxysilyl group; and, (viii) possesses from 3 to about 20 silane units of which from 1 to about 10 are mercaptosilane units and from 1 to about 10 are hydrocarbylsilane and/or heterocarbylsilane units, the terminal silane units independently possessing one or two hydroxyalkoxysilyl groups and/or a cyclic dialkoxysilyl group. In another embodiment herein there is provided a mercaptofunctional silane composition as described herein wherein in each mixture, the ratio of mercaptan to hydrocarbyl group and/or heterocarbyl group ranges from about 20:1 to about 0.05:1.

In one application of this first embodiment of the general preparative process herein, at least one hydrocarbyltrialkoxysilane of Formula (4) is transesterified with at least one diol of Formula (7) or (8), optionally, in the presence of a transesterification catalyst such as the non-limiting example of para-toluenesulfonic acid, to provide organofunctional silane (vii), i.e. the non-limiting example of hydrocarbylsilane oligomer, mercaptotrialkoxysilane of Formula (5) is transesterified with at least one diol of Formula (7) or (8), optionally, in the presence of a transesterification catalyst such as the non-limiting example of para-toluenesulfonic acid, to provide organofunctional silane (vi), i.e. the non-limiting example of mercaptosilane oligomer, which is then mixed with organofunctional silane (vii) and subjected to further transesterification, optionally, in the presence of transesterification catalyst, to yield one or more, organofunctional silanes (viii), i.e. the non-limiting example of silane oligomer containing one or more mercaptosilanes and one or more hydrocarbylsilanes, alone or in combination with one or more other organofunctional silanes (i)-(v).

In a third embodiment of the general preparative procedure herein, at least one mercaptosilane of Formula (3) in admixture with at least one hydrocarbylsilane of Formula (1) and/or heterocarbylsilane of Formula (2) are transesterified with at least one polyhydroxy-containing compound of Formula (6), optionally, in the presence transesterification catalyst, to provide, inter alia, one or more organofunctional silanes (v) and/or (viii), and/or other mixtures of organofunctional silanes, e.g. the non-limiting examples of a mixture of silanes (i) and (ii); (i) and (v); (i), (ii) and (v); (ii) and (viii); (ii), (v) and (viii); (i), (ii), (v) and (viii), and the like.

In one application of the foregoing third embodiment of the general preparative process, at least one mercaptotrialkoxysilane of Formula (5) and at least one heterocarbyltrialkoxysilane of Formula (4) are transesterified together with at least one diol of Formula (7), optionally, in the presence of transesterification catalyst, to provide one or more silanes (v) and/or (viii).

In a fourth embodiment of the general preparative process, at least one mercaptosilane of Formula (3) is transesterified with at least one polyhydroxy-containing compound of Formula (6), optionally, in the presence of transesterification catalyst, to provide at least one dimer (iii) and/or oligomer (vi), or mercaptosilane (i) alone or in admixture with dimer (iii) and/or oligomer (iv).

In one application of the foregoing fourth embodiment of the general preparative process, at least one mercaptotrialkoxysilane of Formula (5) is transesterified with at least one diol of Formula (7), optionally, in the presence of transesterification catalyst, to provide mercaptosilane dimer (iii) and/or oligomer (vi).

In one embodiment, it is also to be understood herein that part or all of the esterification product(s) obtained from one of the afore-described process embodiments can be combined with part or all of the product(s) obtained from one of the other process embodiments. Thus, in one non-limiting example, hydrocarbylsilane and/or heterocarbylsilane dimer (iv) and/or hydrocarbylsilane and/or heterocarbylsilane oligomer (vii) resulting from the first preparative procedure can be admixed with mercaptosilane dimer (iii) and/or mercaptosilane oligomer (vi) to provide a mixture of organofunctional silanes possessing both mercaptan and hydrocarbyl and/or heterocarbyl functionalities. In another embodiment, in a similar manner, simple mixing of the esterified product(s) of one particular embodiment of the general preparative process can be admixed with the esterified product(s) of another embodiment of the general preparative process to provide still other compositions within the scope of the invention possessing both mercaptan and hydrocarbyl and/or heterocarbyl functionality.

In one embodiment, reaction conditions for the process of preparing organofunctional silanes (i)-(viii) and their mixtures include molar ratios of silane(s), determined by adding the individual molar contribution of silanes of Formulae (1), (2) and (3), and polyhydroxy-containing compound(s) of Formula (6) of specifically from about 0.1 to about 3 moles of compound of Formula (6) per mole of silyl group, more specifically from about 0.5 to about 2 moles of compound of Formula (6) per mole of silyl group, and most specifically from about 1 to about 1.5 moles of Formula (6) per mole of silyl group, determined by adding the individual contribution of silanes of Formulae (1), (2) and (3), a temperature of from about 0° C. to about 150° C., a pressure of from about 0.1 to about 2,000 mmHg, and in the optional presence of catalyst, solvent, and the like.

In a specific embodiment herein, an mercaptofunctional and cyclic and/or bridging dialkoxy silane composition is provided comprising at least one silane selected from the group consisting of:

$$[G^1(SiX^\alpha{}_u Z^\beta{}_v Z^\theta{}_w)_s]_m[(HS)_r—G^2—(SiX^\alpha{}_u Z^\beta{}_v Z^\theta{}_w)_s]_n \quad (10)$$

and $$[[G^3—(YG^2)_kY]_jG^2—(SiX^\alpha{}_u Z^\beta{}_v Z^\theta{}_w)_s]_m[(HS)_r— \\ G^2—(SiX^\alpha{}_u Z^\beta{}_v Z^\theta{}_w)_s]_n \quad (11)$$

wherein:

each occurrence of Y is independently selected from a polyvalent species $(—Q)_a[C(=E)]_b(A—)_c$, wherein the atom (E) is attached to an unsaturated carbon atom;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of $G^3$ is independently selected from the group consisting of monovalent and polyvalent groups derived by substitution of alkyl, alkenyl, aryl, or aralkyl wherein $G^3$ can have from 1 to about 30 carbon atoms, with the proviso that if $G^3$ is monovalent, $G^3$ can be hydrogen;

each occurrence of $X^\alpha$ is independently selected from the group consisting of —Cl, —Br, RO—, RC(=O)O—, $R_2C=NO—$, $R_2NO—$, $R_2N—$, —R, $(HO)_{d-1}G^4O—$, $HO(CR^O{}_2)_fO—$, and $HO(CR^O{}_2CR^O{}_2)_e—$, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^4$ is independently a substituted hydrocarbon group from 2 to about 15 carbon atoms or a substituted heterocarbon group from about 4 to about 15 carbon atoms and contains one or more etheric oxygen atoms, $R^O$ is independently given by one of the members listed for R, f is 2 to about 15 and e is 2 to about 7;

each occurrence of Q is independently selected from the group consisting of oxygen, sulfur, and (—NR—) and with the proviso that when Q is sulfur, b is 0;

each occurrence of A is independently selected from the group consisting of oxygen, sulfur, and (—NR—) and with the proviso that when A is sulfur, b is 0;

each occurrence of E is independently selected from the group consisting of oxygen, sulfur, and (—NR—);

each occurrence of $Z^\beta$, which forms a bridging structure between two silicon atoms, is independently selected from the group consisting of, $[—OG^4(OH)_{d-2}O—]_{0.5}$, $[—O(CR^O{}_2CR^O{}_2O)_e—]_{0.5}$ and $[—O(R^OCR^O)_fO—]_{0.5}$, wherein each occurrence of $R^O$ is independently given by one of the members listed above for R; and, each occurrence of $G^4$ is independently selected form the group consisting of a substituted hydrocarbon group from 2 to 15 carbon atoms or a substituted hetercarbon from 4 to 15 carbon atoms and contain one or more etheric oxygen atoms;

each occurrence of $Z^\theta$, which forms a cyclic structure with a silicon atom, is independently given by —$OG^4$ $(OH)_{d-2}O—$, —$O(CR^O{}_2CR^O{}_2O)_e$— and —$O(R^OCR^O)_fO—$ wherein each occurrence of $R^O$ is independently given by one of the members listed above for R;

each occurrence of the subscripts, a, b, c, d, e, f, j, k, m, n, r, s, u, v and w are integers independently given by a is specifically 0 or 1, and more specifically 1; b is specifically 0 or 1, and more specifically 0; c is specifically 0 or 1, and more specifically 0; d is specifically from about 2 to about 8, more specifically from about 2 to about 4 and most specifically about 2; e is specifically from about 2 to about 7, more specifically from about 2 to about 4 and most specifically about 2; f is specifically from about 2 to about 15, more specifically from about 2 to about 4 and most specifically about 3; j is specifically from 1 to about 3, more specifically 1 to about 2 and most specifically 1; k is specifically from 0 to about 15, more specifically from about 0 to about 5, and most specifically from about 0 to about 2; m is specifically from about 1 to about 20, more specifically from about 1 to about 5 and most specifically from about 2 to about 4; n is specifically from about 1 to about 20, more specifically from about 1 to about 5 and most specifically from about 2 to about 4; r is specifically from 1 to about 3, and more specifically about 1; and s is specifically from 1 to about 3, and more specifically about 1; u is specifically from 0 to 3, more specifically from about 0 to about 2, and most specifically from about 0 to about 1; v is specifically from 0 to 3, more specifically from about 0 to about 2, and most specifically from about 0 to about 1; w is specifically from 0 to about 1, and more specifically about 1; with the proviso that u+v+2w=3; and with the proviso that the each of the above structures (10) and/or (11) contains at least one hydrolysable group, $Z^\beta$ or $Z^\theta$.

In one embodiment it is understood that the structure, $[—OG^4(OH)_{d-2}(O—)]_{0.5}$ can further react with a third or more silyl groups to form bridging trialkoxysilyl, tetraalkoxysilyl groups and so on, and are represented by $[—OG^4 (OH)_{d-3}(O—)_2]_{1/3}$, $[—OG^4(OH)_{d-4}(O—)_3]_{1/4}$ and so on, respectively.

In another embodiment herein, the ratio of m to n is specifically from about 20:1 to about 0.05 to 1, more specifically from about 5:1 to about 0.2:1, and most specifically from about 2:1 to about 0.5:1.

In accordance with another embodiment herein, a process for the preparation of an mercaptofunctional silane containing hydroxyalkyloxysilyl groups, cyclic and/or bridging dialkoxysilyl groups and hydrocarbyl and/or heterocarbyl functionality groups is provided which comprises blending at least one hydrocarbyl functional silane of the formula:

$$G^1—(SiX_3)_3 \quad (1)$$

and/or heterocarbyl functional silane of the formula:

$$[G^3—(YG^2)_kY]_j—G^2—(SiX_3)_s \quad (2)$$

with at least one mercaptofunctional silane of the formula:

$$(HS)_r—G^2—(SiX_3)_s \quad (3)$$

wherein each occurrence of $G^1$, $G^2$, $G^3$, Y, X, j, k, r, and s have one of the aforestated meanings and with the proviso that at least one of X is a hydrolyzable group; and transesterifying the mixture with one or more polyhydroxy-containing compounds of the general formula (6):

$$G^4(OH)_d \quad (6)$$

wherein each occurrence of $G^4$ and d have one of the aforestated meetings; and advantageously in the presence of a transesterification catalyst.

In still another embodiment herein, a process for the preparation of an mercaptofunctional silane containing cyclic and/or bridging dialkoxy silyl groups and hydrocarbyl and/or heterocarbyl functionality is provided which comprises blending at least one hydrocarbyl functional silane of the formula:

$$G^1—(SiX_3)_3 \quad (1)$$

and/or heterocarbyl functional silane of the formula:

$$[G^3-(YG^2)_kY]_j-G^2-(SiX_3)_s \quad (2)$$

with at least one mercaptofunctional silane of the formula:

$$(HS)_r-G^2-(SiX_3)_s \quad (3)$$

wherein each occurrence of $G^1$, $G^2$, $G^3$, Y, X, j, k, r, and s have one of the aforestated meanings and with the proviso that at least one of X is a hydrolyzable group, and transesterifying the mixture with one or more diols of the general Formulae (7) and (8):

$$HO(R^oCR^o)_fOH \quad (7)$$

$$HO(CR^o{}_2CR^o{}_2O)_eH \quad (8)$$

wherein $R^o$, e, and f have one of the aforestated meanings. In still another embodiment, the diol is $HO(R^oCR^o)_fOH$ wherein $R^o$ and f have one of the aforestated meetings.

In one embodiment herein in connection with silanes of Formulae (10) and (11), the terms "diol" and "difunctional alcohol" refer to any structure of the general Formula (7):

$$HO(R^oCR^o)_fOH \quad (7)$$

wherein f and $R^o$ are as defined herein. In one embodiment, these structures represent hydrocarbons in which two hydrogen atoms are replaced with —OH in accordance with compounds of Formula (7), supra.

In another embodiment herein in connection with silanes of Formulae (10) and (11), "dialkoxy" and "difunctional alkoxy" refer to hydrocarbon-based diols in which the two OH hydrogen atoms have been removed to give divalent radicals, and whose structures are represented by the general formula:

$$-O(R^oCR^o)_fO- \quad (12)$$

wherein f and $R^o$ are as defined herein.

In yet another embodiment herein in connection with silanes of Formulae (10) and (11), "cyclic dialkoxy" refers to a silane or group in which cyclization is about a silicon atom by two oxygen atoms each of which is attached to a common divalent hydrocarbon group such as is commonly the case with diols. In one embodiment cyclic dialkoxy groups herein are represented by $Z^\theta$. In one embodiment the structure of $Z^\theta$ is important in the formation of the cyclic structure. In yet one more embodiment $R^o$ groups that are more sterically hindered than hydrogen promote the formation of cyclic structures. In yet even one more embodiment the formation of cyclic structures is also promoted when the value of f in diol of Formula (7) is 2 or 3, and more specifically 3.

In yet a further embodiment herein in connection with silanes of Formulae (10) and (11), "bridging dialkoxy" refers to a silane or group in which two different silicon atoms are each bound to one oxygen atom, which in turn is bound to a common divalent hydrocarbon group such as is commonly found in diols. Bridging dialkoxy groups herein are represented by $Z^\beta$. In yet still a further embodiment herein in connection with silanes of Formulae (10) and (11), "hydroxyalkoxy" refers to a silane or group in which one OH hydrogen atom has been removed to provide a monovalent radical, and whose structures are represented by the general Formulae (13), (14) and (15):

$$(HO)_{d-1}G^4O- \quad (13)$$

$$HO(R^oCR^o)_fO- \quad (14)$$

$$HO(CR^o{}_2CR^o{}_2O)_e- \quad (15)$$

wherein $G^4$, e, f and $R^o$ are defined herein. Hydroxyalkoxy groups herein are represented by $X^\alpha$.

In yet even another embodiment herein in connection with silanes of Formula (10) and (11), the term "hydrocarbon based diols" refers to diols that contain two OH groups as part of a hydrocarbon structure. In another embodiment, absent from these hydrocarbon based diols are heteroatoms (other than the oxygens in the OH groups), in particular ether groups. In one embodiment, hydrocarbon diols that contain heteroatoms, such as oxygen, are represented by the Formula (8):

$$HO(CR^o{}_2CR^o{}_2O)_e-H \quad (8).$$

In another embodiment, these diols are not as likely to form cyclic structures with the silyl group because of the size of the ring being 8 atoms or larger, which are less likely to form than rings that contain 5 or 6 atoms.

In yet an even further embodiment structure of Formula (7) will be referred to herein as either "the appropriate diol" or "glycol" prefixed by the particular hydrocarbon group associated with the two OH groups. In one specific embodiment, some non-limiting examples of Formula (7) include neopentylglycol, 1,3-butanediol, 2-methyl-1,3-propanediol and 2-methyl-2,4-pentanediol.

In yet even another specific embodiment, structure of Formula (12) will be referred to herein as the appropriate dialkoxy, prefixed by the particular hydrocarbon group associated with the two OH groups. In one specific embodiment, thus, for example, the diols, neopentylglycol, 1,3-butanediol, and 2-methyl-2,4-pentanediol correspond herein to the dialkoxy groups, neopentylglycoxy, 1,3-butanedialkoxy, 2-methyl-1,3-propanediol and 2-methyl-2,4-pentanedialkoxy, respectively.

In a further embodiment herein for $Z^\beta$, the notations, $[-OG^4(OH)_{d-2}O-]_{0.5}$, $[-O(R^oCR^o)_fO-]_{0.5}$, and $[-O(CR^o{}_2CR^o{}_2O)_e-]_{0.5}$ refer to one-half of a bridging dialkoxy group which can connect to different silyl groups present in the mercaptofunctional silanes of Formulae (10) and (11). In one embodiment, these notations are used in conjunction with a silicon atom and they are taken herein to mean that one-half of a dialkoxy group is bound to the particular silicon atom. It is understood that the other half of the dialkoxy group is bound to a silicon atom that occurs somewhere else in the overall molecular structure being described. Thus, in one embodiment, the $[-OG^4(OH)_{d-2}O-]_{0.5}$, $[-O(R^oCR^o)_fO-]_{0.5}$, and $[-O(CR^o{}_2CR^o{}_2O)_e-]_{0.5}$ dialkoxy groups mediate the chemical bonds that hold two separate silicon atoms together, whether these two silicon atoms occur intermolecularly or intramolecularly. In one embodiment, in the case of $[-O(R^oCR^o)_fO-]_{0.5}$ and $[-O(CR^o{}_2CR^o{}_2)_e-]_{0.5}$, if the group $(R^oCR^o)_f$ and $(CR^o{}_2CR^o{}_2O)_e$ are unsymmetrical, either end of $[-O(R^oCR^o)_fO-]_{0.5}$ and $[-O(CR^o{}_2CR^o{}_2O)_e-]_{0.5}$ can be bound to either of the two silicon atoms required to complete the structures of silanes of Formulae (10) and (11).

In a still further embodiment herein in connection with silanes of Formulae (1), (2), (3), (10) and (11), "alkyl" includes straight, branched and cyclic alkyl groups; "alkenyl" includes any straight, branched, or cyclic alkenyl group containing one or more carbon-carbon double bond, where the point of substitution can be either at a carbon-carbon double bond or elsewhere in the group; and "alkynyl" includes any straight, branched, or cyclic alkynyl group containing one or more carbon-carbon triple bonds and, optionally, one or more carbon-carbon double bonds as well, where the point of substitution can be either at a carbon-carbon triple bond, a carbon-carbon double bond, or elsewhere in the group. Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of alkynyls include, but are not limited to, acetylenyl, propargyl and methylacetylenyl.

In one embodiment herein in connection with silanes Formulae (1), (2), (3), (10) and (11), "aryl" includes the non-limiting group of any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents; and "arenyl" includes the non-limiting group of any of the aforementioned aryl groups in which one or more hydrogen atoms have been substituted by the same number of like and/or different alkyl (as defined herein) substituents. Specific examples of aryls include, but are not limited to, phenyl and naphthalenyl. Specific examples of aralkyls include, but are not limited to, benzyl and phenethyl. Specific examples of arenyls include, but are not limited to, tolyl and xylyl.

In another embodiment herein, in connection with silanes of Formulae (1), (2), (3), (10) and (11), "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples of "cyclic alkyl", "cyclic alkenyl", and "cyclic alkynyl" include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

In one embodiment some representative examples of the functional groups (—Y—) present in the silanes of the present invention include, but are not limited to, carboxylate ester, —C(=O)—O— and —OC(=O)— (any silane with this functional group is a "carboxylate ester silane"); ketone, —C(=O)— (any silane with this functional group is a "ketonic silane"; thioketone, —C(=S)— (any silane with this functional group is a "thioketonic silane"); carbonate ester, —O—C(=O)—O— (any silane with this functional group is a "carbonate ester silane"); amide, —C(=O)NR— and —NRC(=O)— (any silane with this functional group is a "amidosilane"); ether, —O— (any silane with this functional group is a "ether silane"); amine, —NR— (any silane with this functional group is a "aminosilane"); urea, —NRC(=O)NR— (any silane with this functional group is a "ureidosilane"); thio, —S-(any silane with this functional group is a "sulfidosilane"); and guanidine, (—NR)C(=NR)NR— (any silane with this functional group is a "guanidinosilane"). In another embodiment herein, each occurrence of Y is selected independently from the group consisting of —C(=NR)—; —(C=O)—; (—NR)C(=O)—; —OC(=O)—; —OC(=S)—; —OC(=O)O—; —C(=S)—; —C(=O)O—; (—NR)C(=O)(NR—); (—NR)C(=NR)(NR—); —O—; —S—; —SS—; and —NR—. In still another embodiment herein, Y is a non-limiting selection, selected from the group consisting of —O—; —NR—; —C(=O)O—; —C(=O)NR— and (—NR)C(=O)(NR—).

In another embodiment herein, the silane is one described by Formula (11) in which Y is —O— or —NR—, $G^2$ is a divalent or polyvalent group derived by substitution of $C_1$-$C_{12}$ alkyl; $G^3$ is hydrogen or $C_1$ to $C_{12}$ straight chain alkyl; $Z^\beta$ is [—O(R$^\circ$CR$^\circ$)$_f$O—]$_{0.5}$ and $Z^\Theta$ is —O(R$^\circ$CR$^\circ$)$_f$O— wherein R$^\circ$ is hydrogen or methyl and f is 2 or 3, m and n are 1 to about 5, k is 1 to about 5, j is 1 and r is 1 to about 2.

In still another embodiment herein, the silane is one described by Formula (10) in which $G^1$ is a monovalent straight chain group derived from a $C_3$-$C_{10}$ alkyl, and $G^2$ is a divalent or polyvalent group derived by substitution of a $C_1$-$C_{10}$ alkyl, $Z^\beta$ is [—O(R$^\circ$CR$^\circ$)$_f$O—]$_{0.5}$ and $Z^\Theta$ is —O(R$^\circ$CR$^\circ$)$_f$O— wherein R$^\circ$ is hydrogen or methyl and f is 2 or 3, m and n are 1 to about 5 and r is 1 to about 2.

In yet another embodiment herein, silane is one in which both the silanes of Formulae (10) and (11) are present; such as wherein both the silanes of Formulae (10) and (11) are mixed together.

In one embodiment some representative examples of $G^1$ include, but are not limited to, $CH_3(CH_2)_g$—, wherein g is 1 to about 29; benzyl; 2-phenylethyl; cyclohexyl; any of the isomers of —$CH_2CH_2$-norborane; any of the isomers of —$CH_2CH_2$-cyclohexane; branched alkyl groups of 1 to 30 carbon atoms and include the non-limiting examples such as $CH_3(CH_2)_4$ $CH(CH_2CH_3)CH_2$—, $CH_3CH_2CH(CH_2CH_3)CH_2$—, $CH_3CH(CH_3)CH_2$—, $CH_3CH_2CH(CH_3)CH_2$—, and $CH_3(CH_2)_4CH(CH_3)CH_2$—;

and any of the monoradicals obtainable from norbornane, cyclohexane, cyclopentane, tetrahydrodicyclopentadiene, or cyclododecene by loss of one hydrogen atom.

In one specific embodiment some representative examples of $G^2$ include, but are not limited to those selected from the group consisting of diethylene cyclohexane; 1,2,4-triethylene cyclohexane; phenylene; any of the structures derivable from divinylbenzene, such as the non-limiting examples of —$CH_2CH_2(C_6H_4)CH_2CH_2$— and —$CH_2CH_2(C_6H_4)CH(CH_3)$—, where the notation $C_6H_4$ denotes a disubstituted benzene ring; any of the structures derivable from dipropenylbenzene, such as the non-limiting examples of —$CH_2CH(CH_3)(C_6H_4)CH(CH_3)CH_2$—, where the notation $C_6H_4$ denotes a disubstituted benzene ring; any of the structures derivable from piperylene, such as the non-limiting examples of —$CH_2CH_2CH_2CH(CH_3)$—, —$CH_2CH_2CH(CH_2CH_3)$—, and —$CH_2CH(CH_2CH_3)$—; any of the isomers of —$CH_2CH_2$-norbornyl-; any of the diradicals obtainable from tetrahydrodicyclopentadiene or cyclododecene by loss of two hydrogen atoms; any of the structures derivable from limonene, such as the non-limiting example of, —$CH_2CH(4$-$CH_3$-$1$-$C_6H_9$—$)CH_3$, where the notation $C_6H_9$ denotes isomers of the trisubstituted cyclohexane ring lacking substitution in the 2 position; any of the monovinyl-containing structures derivable from trivinylcyclohexane, such as the non-limiting examples of —$CH_2CH_2(vinylC_6H_9)CH_2CH_2$— and —$CH_2CH_2(vinylC_6H_9)CH(CH_3)$—, where the notation $C_6H_9$ denotes any isomer of the trisubstituted cyclohexane ring; any of the monounsaturated structures derivable from myrcene containing a trisubstituted C=C, such as the non-limiting examples of

—$CH_2CH[CH_2CH_2CH=C(CH_3)_2]CH_2CH_2$—,

—$CH_2CH[CH_2CH_2CH=C(CH_3)_2]CH(CH_3)$—,

—$CH_2C[CH_2CH_2CH=C(CH_3)_2](CH_2CH_3)$—,

—$CH_2CH_2CH[CH_2CH_2CH=C(CH_3)_2]CH_2$—,

—$CH_2CH_2(C$—$)(CH_3)[CH_2CH_2CH=C(CH_3)_2]$, and

—CH$_2$CH[CH(CH$_3$)[CH$_2$CH$_2$CH=C(CH$_3$)$_2$]]—; and any of the monounsaturated structures derivable from myrcene lacking a trisubstituted C=C, such as the non-limiting examples of

—CH$_2$CH(CH=CH$_2$)CH$_2$CH$_2$CH$_2$C(CH$_3$)$_2$—,

—CH$_2$CH(CH=CH$_2$)CH$_2$CH$_2$CH[CH(CH$_3$)$_2$]—,

—CH$_2$C(=CH—CH$_3$)CH$_2$CH$_2$CH$_2$C(CH$_3$)$_2$—,

—CH$_2$C(=CH—CH$_3$)CH$_2$CH$_2$CH[CH(CH$_3$)$_2$]—,

—CH$_2$CH$_2$C(=CH$_2$)CH$_2$CH$_2$CH$_2$C(CH$_3$)$_2$—,

—CH$_2$CH$_2$C(=CH$_2$)CH$_2$CH$_2$CH[CH(CH$_3$)$_2$]—,

—CH$_2$CH=C(CH$_3$)$_2$CH$_2$CH$_2$CH$_2$C(CH$_3$)$_2$— and

—CH$_2$CH=C(CH$_3$)$_2$CH$_2$CH$_2$CH[CH(CH$_3$)$_2$]; —(CH$_2$)$_g$— wherein g is preferably an integer of from 1 to 30, which represent terminal straight-chain alkyls further substituted terminally at the other end, such as the non-limiting examples of —CH$_2$—, —CH$_2$CH$_2$—, —CH$_2$CH$_2$CH$_2$—, and —CH$_2$CH$_2$CH$_2$CH$_2$CH$_2$CH$_2$CH$_2$CH$_2$—, and their beta-substituted analogs, such as —CH$_2$(CH$_2$)$_i$CH(CH$_3$)—, where i is preferably 0 to 16; methyl substituted alkylene groups such as the non-limiting examples of —CH$_2$CH$_2$-cyclohexyl-, —CH$_2$CH$_2$C(CH$_3$)$_2$CH$_2$—, —CH$_2$CH(CH$_3$)CH$_2$—, any of the structures derivable from isoprene, such as —CH$_2$CH(CH$_3$)CH$_2$CH$_2$—, —CH$_2$CH(CH$_3$)CH(CH$_3$)—, —CH$_2$C(CH$_3$)(CH$_2$CH$_3$)—, —CH$_2$CH$_2$CH(CH$_3$)CH$_2$—, —CH$_2$CH$_2$C(CH$_3$)$_2$— and —CH$_2$CH[CH(CH$_3$)$_2$]—; any structure derivable from methallyl chloride; any of the structures derivable from butadiene, such as the nonlimiting examples of —CH$_2$CH$_2$CH$_2$CH$_2$—, —CH$_2$CH$_2$CH(CH$_3$)—, and —CH$_2$CH(CH$_2$CH$_3$)—; and, any of the diradicals obtainable from norbornane, cyclohexane, or cyclopentane, by loss of two hydrogen atoms.

In another embodiment herein, some representative examples of G$^3$ include, but are not limited to, hydrogen, CH$_3$(CH$_2$)$_g$—, wherein g is 1 to about 29; benzyl; 2-phenylethyl; cyclohexyl; any of the isomers of —CH$_2$CH$_2$-norborane; any of the isomers of —CH$_2$CH$_2$-cyclohexane; branched alkyl groups of 1 to 30 carbon atoms such as the non-limiting examples including CH$_3$(CH$_2$)$_4$CH(CH$_2$CH$_3$)CH$_2$—, CH$_3$CH$_2$CH(CH$_2$CH$_3$)CH$_2$—, CH$_3$CH(CH$_3$)CH$_2$—, CH$_3$CH$_2$CH(CH$_3$)CH$_2$—, CH$_3$(CH$_2$)$_4$CH(CH$_3$)CH$_2$—, and any of the monoradicals obtainable from norbornane, cyclohexane, cyclopentane, tetrahydrodicyclopentadiene, or cyclododecene by loss of one hydrogen atom.

In another embodiment herein, the silanes of Formula (10) and (11) have structures in which the sum of the carbon atoms in the hydrocarbyl and/or heterocarbyl groups that are determined by adding up the carbon atoms in the G$^1$, G$^2$ and G$^3$ groups is specifically from about 3 to about 18 more specifically from about 6 to about 14, and most specifically of from about 8 to about 12. In one embodiment, the amount of carbon in these fragments facilitates the dispersion of filler into the organic polymers, thereby improving the balance of properties in the cured filled rubber.

In yet another embodiment herein, G$^1$ is CH$_3$CH$_2$CH$_2$CH$_2$CH$_2$CH$_2$CH$_2$— and G$^2$ is —CH$_2$CH$_2$CH$_2$—, r is 1 and s is 1.

In yet a further embodiment, some representative non-limiting examples of R and R$^\circ$ groups are hydrogen, branched and straight-chain alkyls of 1 to 18 carbon atoms or more, such as the non-limiting examples of methyl, ethyl, propyl, isopropyl, butyl, octenyl, cyclohexyl, phenyl, benzyl, tolyl and allyl.

In one embodiment, R groups are selected from C$_1$ to C$_4$ alkyls and hydrogen and R$^\circ$ groups are selected from hydrogen, methyl, ethyl and propyl.

In one other embodiment, some specific non-limiting examples of X$^\alpha$ are methoxy, ethoxy, isobutoxy, propoxy, isopropoxy, acetoxy, oximato, monovalent hydroxyalkoxy groups derived from diols, —O(R$^\circ$CR$^\circ$)$_f$OH where R$^\circ$ and f is defined as herein, such as the non-limiting examples of 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydroxybut-1-oxy and monovalent ether alkoxy groups of the general Formulae (16), (17), and (18):

  (16)

  (17)

  (18)

wherein R$^1$ is independently selected from the group consisting of straight, cyclic or branched alkyl groups that can or can not contain unsaturation, alkenyl groups, aryl groups and aralkyl groups that contain from 1 to 18 carbon atoms; and R$^\circ$, G$^4$, e and f are defined as herein. In one embodiment X$^\alpha$ can also be a monovalent alkyl group, such as the non-limiting examples of methyl and ethyl.

In a specific embodiment, X$^\alpha$ is one of the non-limiting examples of methoxy, ethoxy, acetoxy, methyl, ethyl, 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydroxybut-1-oxy.

In one embodiment, some specific non-limiting examples of Z$^\beta$ and Z$^\Theta$ are the divalent alkoxy groups derived from diols such as ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol and pinacol. In another embodiment, some more specific non-limiting examples of Z$^\beta$ and Z$^\Theta$ are divalent alkoxy groups derived from ethylene glycol, propylene glycol, neopentyl glycol, 1,3-propanediol, 2-methyl-1,3-propanediol, 1,3-butanediol and 2-methyl-2,4-pentanediol.

In one specific embodiment herein, Z$^\beta$ and Z$^\Theta$ are divalent alkoxy groups derived from 1,3-propanediol, 2-methyl-1,3-propanediol, 1,3-butanediol, and 2-methyl-2,4-pentanediol and combinations thereof. In one embodiment, the cyclic dialkoxy content of the silanes herein should be kept sufficiently high relative to the total dialkoxy content present to prevent excessive crosslinking, which would lead to gellation. In one embodiment herein, the cyclic dialkoxy silyl content of the silanes can specifically be from about 10 to about 100 mole percent of the total concentration of silyl groups, more specifically from about 25 to about 90 mole percent of the total concentration of silyl groups and most specifically from about 50 to about 70 mole percent of the total concentration of silyl groups. In another embodiment herein, excessive crosslinking can also be avoided if X$^\alpha$ in the structure of Formulae (10) and (11), as indicated by the coefficient u, is large, such as for example, specifically, from about 1 to about 2. In one embodiment, v and w in Formulae (10) and (11) are such that the ratio v/w is specifically between 0 and 1. In another embodiment, u is from 1 to about 2 with the proviso that u+v+2w=3.

In yet a further embodiment, some representative non-limiting examples of the mercaptofunctional silanes herein, such as those that contain cyclic and/or bridging dialkoxysilyl groups, mercapto groups and hydrocarbylsilane and/or heterocarbylsilane include, but are not limited to, 3-{4-methyl-2-[2-(4-methyl-2-pentyl-[1,3,2]dioxasilolan-2-yloxy)-propoxy]-[1,3,2]dioxasilolan-2-yl}-propane-1-thiol; 3-{2-[2-(2-methyl-[1,3,2]dioxasilolan-2-yloxy)-ethoxy]-[1,3,2]dioxasilolan-2-yl}-propane-1-thiol; mixture of 3-[2-(3-mercapto-propyl)-[1,3,2]dioxasilinan-2-yloxy]-propan-1-ol and 3-(2-butyl-[1,3,2]dioxasilinan-2-yloxy)-propan-1-ol; 4-{2-[3-(2-butyl-[1,3,2]dioxasilinan-2-yloxy)-propoxy]-[1,3,2]dioxasilinan-2-yl}-butane-1-thiol; 4-[2-(3-{2-[3-(2-methoxy-ethoxy)-propyl]-[1,3,2]dioxasilinan-2-yloxy}-propoxy)-[1,3,2]dioxasilinan-2-yl]-butane-1-thiol; 4-[5-methyl-2-(2-methyl-3-{5-methyl-2-[3-(2-methylamino-ethylamino)-propyl]-[1,3,2]dioxasilinan-2-yloxy}-propoxy)-[1,3,2]dioxasilinan-2-yl]-butane-1-thiol; 2-acetylamino-N-[3-(2-{3-[2-(4-mercapto-butyl)-5-methyl-[1,3,2]dioxasilinan-2-yloxy]-2-methyl-propoxy}-5-methyl-[1,3,2]dioxasilinan-2-yl)-propyl]-acetamide; (2-{3-[3-(2-{3-[2-(4-mercapto-butyl)-5-methyl-[1,3,2]dioxasilinan-2-yloxy]-2-methyl-propoxy}-5-methyl-[1,3,2]dioxasilinan-2-yl)-propyl]-ureido}-ethyl)-urea; 4-acetoxy-butyric acid 3-(2-{3-[2-(4-mercapto-butyl)-5,5-dimethyl-[1,3,2]dioxasilinan-2-yloxy]-2,2-dimethyl-propoxy}-5,5-dimethyl-[1,3,2]dioxasilinan-2-yl)-propyl ester; carbonic acid 2-[3-(2-{3-silanyl)-2-methyl-propan-1-ol; 4-(benzyl-(3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-phenethyl-silanyloxy]-2-methyl-propoxy}-(3-mercapto-propyl)-silanyl]-2-methyl-butoxy}-silanyl)-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]oxasilolan-2-yloxy)-propoxy]-silanyl}-2-methyl-butoxy)-pent-4-enyl-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]oxasilolan-2-yloxy)-propoxy]-silanyl}-2-methyl-butoxy)-(3-mercapto-propyl)-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]oxasilolan-2-yloxy)-propoxy]-silanyl}-2-methyl-butoxy)-(3-mercapto-propyl)-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-octyl-[1,2]oxasilolan-2-yloxy)-propoxy]-silanyl}-2-methyl-butoxy)-(3-mercapto-propyl)-silanyl]-2-methyl-butan-1-ol; and combinations thereof.

In an even further embodiment herein, organofunctional silane compositions herein that contain cyclic and/or bridging silyl groups and both mercaptan and hydrocarbyl and/or heterocarbyl groups normally have a random distribution of mercapto and hydrocarbyl and/or heterocarbyl groups within the individual silane. However, in one specific embodiment herein silanes can be prepared in which the mercaptan groups are segregated. In a more specific embodiment this segregation will result in compositions where the nearest neighbors to a mercaptan group are other mercaptan groups or the nearest neighbors to a hydrocarbyl and/or heterocarbyl group are [2-(4-mercapto-butyl)-5,5-dimethyl-[1,3,2]dioxasilinan-2-yloxy]-2,2-dimethyl-propoxy}-5,5-dimethyl-[1,3,2]dioxasilinan-2-yl)-propoxycarbonyloxy]-ethyl ester methyl ester; 4-{[3-(2-dodecyl-4,4,6-trimethyl-[1,3,2]dioxasilinan-2-yloxy)-1,1-dimethyl-butoxy]-dimethyl-silanyl}-butane-1-thiol; 4-{[3-(2-dodecyl-4,4,6-trimethyl-[1,3,2]dioxasilinan-2-yloxy)-1,1-dimethyl-butoxy]-diethoxy-silanyl}-butane-1-thiol; 4-[butyl-[3-(2-dodecyl-4,4,6-trimethyl-[1,3,2]dioxasilinan-2-yloxy)-1,1-dimethyl-butoxy]-(4-mercapto-butyl)-silanyloxy]-2-methyl-pentan-2-ol; 4-{(3-hydroxy-2-methyl-propoxy)-(4-mercapto-butyl)-[2-methyl-3-(5-methyl-2-octyl-[1,3,2]dioxasilinan-2-yloxy)-propoxy]-silanyl}-2-methyl-butan-1-ol; 3-{(3-hydroxy-2-methyl-propoxy)-(4-mercapto-butyl)-[2-methyl-3-(5-methyl-2-octyl-[[1,3,2]dioxasilinan-2-yloxy)-propoxy]-silanyloxy}-2-methyl-propan-1-ol; 4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(4-mercapto-butyl)-silanyl]-2-methyl-butan-1-ol; 3-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(4-mercapto-butyl)-silanyloxy]-2-methyl-propan-1-ol; 3-[{3-[(3-hydroxy-2-methyl-propoxy)-{4-[(3-hydroxy-2-methyl-propoxy)-methyl-octyl-silanyloxy]-3-methyl-butyl}-(3-mercapto-propyl)-silanyloxy]-2-methyl-propoxy}-(3-hydroxy-2-methyl-propyl)-octyl-silanyloxy]-2-methyl-propan-1-ol; 4-((3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(3-mercapto-propyl)-silanyl]-2-methyl-butoxy}-octyl-silanyl)-2-methyl-butan-1-ol; 3-((3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(3-mercapto-propyl)-silanyl]-2-methyl-butoxy}-octyl- other hydrocarbyl and/or heterocarbyl groups. In one specific embodiment, the segregation of the mercaptan groups can occur when hydrocarbyl and/or heterocarbyl cyclic and/or bridged silanes are physically mixed with mercaptofunctional cyclic and/or bridged silanes.

Moreover, in one other embodiment herein, it is understood that these silane compositions can also contain mercaptofunctional and hydrocarbyl and/or heterocarbyl silane components that contain only monofunctional alkoxy groups. In a further embodiment herein, mercaptofunctional silanes, hydrocarbylsilane and/or heterocarbylsilane containing only monofunctional alkoxy groups can be used as reagents in the preparation of the silanes herein. However, it is understood in one embodiment that these monofunctional alkoxy groups can contribute to VOC emissions during use if the monofunctional alcohols that are form upon hydrolysis of the silanes have high vapor pressure at room temperature. In a further embodiment, some non-limiting examples of high boiling monofunctional alkoxy groups, are those such as the alkoxy groups whose structures are represented by formula

$$R^1O(CR^0{}_2CR^0{}_2O)_e— \qquad (18)$$

wherein $R^0$, $R^1$ and e are defined as herein. In another embodiment, moreover, it is understood that the partial hydrolyzates and/or condensates of these cyclic and/or bridging mercaptofunctional and hydrocarbyl and/or heterocarbyl silanes (i.e., cyclic and/or bridging dialkoxy mercaptofunctional and hydrocarbyl or heterocarbyl siloxanes and/or silanols) can also be encompassed by the silanes herein, in that these partial hydrolyzates and/or condensates will be a side product of most methods of manufacture of the silanes described herein or can occur upon storage, especially in humid conditions, or under conditions in which residual water remaining from their preparation is not completely removed subsequent to their preparation.

Furthermore in another specific embodiment, partial to substantial hydrolysis of silanes of Formula (10) and (11) will form silanes that contain siloxane bonds, i.e., $Z^\beta=(-O-)_{0.5}$, and are encompassed by the silanes described herein; and in a more specific embodiment they can be deliberately prepared by incorporating the appropriate stoichiometry or an excess of water into the methods of preparation described herein for the silanes. In one embodiment, silane structures herein encompassing hydrolyzates and siloxanes are described in the structures represented by Formulae (10) and (11) wherein the subscripts, v, of $Z^\beta=(-O-)_{0.5}$ and/or u of $X^\alpha=OH$ are substantive (i.e., substantially larger than zero), for example, where v is specifically of from about 1 to about 2, and more specifically of about 1; and/or wherein u is specifically of from about 0 to about 2, more specifically of from about 0 to about 1 and most specifically of about 1 and with the proviso that the silane of Formulae (10) and (11) contain at least one $Z^\beta$ that is $[-OG_4(OH)_{d-2}O-]_{0.5}$ or at least one $Z^\Theta$ that is $-O(R^0CR^0)_fO-$. In one embodiment herein, the ratio of siloxane bridging group, $(-O-)_{0.5}$, to dioxy bridging group, $[-O(R^0CR^0)_fO-]_{0.5}$, is within a range of from about 0 to about 1. In another embodiment, the ratio is within a range of from about 0 to about 0.2. In a further embodiment, the ratio is within a range of from about 0.05 to about 0.15.

In another embodiment herein, the organofunctional silanes herein, including their mixtures, can be loaded on a particulate carrier such as the non-limiting examples of a porous polymer, carbon black, a siliceous material such as silica, and the like, so that they are in solid form for addition to rubber in a rubber compounding operation.

In one embodiment herein there is provided a process for making a mercaptofunctional silane composition which comprises:

reacting at least one mercapto functional silane possessing at least one transesterifiable silyl group and at least one hydrocarbylsilane and/or heterocarbylsilane possessing at least one transesterifiable silyl group, with at least one polyhydroxy-containing compound under transesterification conditions to provide said mercaptofunctional silane composition wherein said mercaptofunctional silane composition contains at least one organofunctional silane selected from the group consisting of:

(i) mercaptosilane possessing at least one hydroxyalkoxysilyl group and/or a cyclic dialkoxysilyl group, (ii) hydrocarbylsilane or heterocarbylsilane possessing at least one hydroxyalkoxysilyl group and/or a cyclic dialkoxysilyl group, (iii) mercaptosilane dimer in which the silicon atoms of the mercaptosilane units are bonded to each other through a bridging dialkoxy group, each silane unit optionally possessing at least one hydroxyalkoxysilyl group and/or a cyclic dialkoxysilyl group, (iv) hydrocarbylsilane and/or heterocarbylsilane dimer in which the silicon atoms of the hydrocarbylsilane and/or heterocarbylsilane units are bonded to each other through a bridging dialkoxy group, each silane unit optionally possessing at least one hydroxyalkoxysilyl group and/or a cyclic dialkoxysilyl group, (v) silane dimer possessing a mercaptosilane unit, the silicon atom of which is bonded to the silicon atom of a hydrocarbylsilane or heterocarbylsilane unit through a bridging dialkoxy group, each silane unit optionally possessing at least one hydroxyalkoxysilyl group and/or a cyclic dialkoxysilyl group, (vi) mercaptosilane oligomer in which the silicon atoms of adjacent mercaptosilane units are bonded to each other through a bridging dialkoxy group, the terminal mercaptosilane units possessing at least one hydroxyalkoxysilyl group and/or a cyclic dialkoxysilyl group, (vii) hydrocarbylsilane and/or heterocarbylsilane oligomer in which the silicon atoms of adjacent hydrocarbylsilane or heterocarbylsilane units are bonded to each other through a bridging dialkoxy group, the terminal hydrocarbylsilane and/or heterocarbylsilane units possessing at least one hydroxyalkoxysilyl group and/or a cyclic dialkoxysilyl group, and (viii) silane oligomer possessing at least one mercaptosilane unit and at least one hydrocarbylsilane or heterocarbylsilane unit, the silicon atoms of adjacent silane units being bonded to each other through a bridging dialkoxy group, the terminal silane units possessing at least one hydroxyalkoxysilyl group and/or a cyclic dialkoxysilyl group, with the provisio that, where the mercaptofunctional silane composition resulting from this process contains one or more of (i), (iii) and (vi), the composition additionally contains one or more of (ii), (iv), (v), (vii) and (viii), and where the mercaptofunctional silane composition resulting from this process contains one or more of (ii), (iv) and (vii), the composition additionally contains one or more of (i), (iii), (v), (vi) and (viii).

In a further embodiment herein, mercaptofunctional silanes of Formulae (10) and (11) herein and mixtures thereof can be prepared by the general preparative process described as herein of which there are numerous specific embodiments. Generally, in one embodiment, the process embodiments for making one or a mixture of silanes of Formulae (10) and (11) involve a transesterification reaction between one or more alkoxysilane Formulae (1), (2) and (3) and one or more polyhydroxy-containing compounds of Formula (6), (7) or (8).

In one embodiment, the process for preparing the mercapto functional silanes of Formula (10) and/or (11) comprises:

a.) mixing hydrocarbyl and/or heterocarbyl silanes of the general Formulae (1) and/or (2):

and/or

with a mercaptosilane of general Formula (3):

wherein each occurrence of $G^1$, $G^2$, $G^3$, Y, X, j, k, r, and s are defined as herein, and with the proviso that at least one of X is a hydrolyzable group, and b.) transesterifying this mixture with at least one diol having the structure $G^4(OH)_d$, $HO(R^0CR^0)_fOH$, or $HO(CR^0{}_2CR^0{}_2O)_e-H$, optionally in the presence of a transesterification catalyst; and removing the X—H group that is formed; wherein each occurrence of $G^4$, $R^0$, d, e and f are defined as herein.

In one embodiment, the first reaction can be carried out by reacting a mixture of mercaptofunctional alkoxy silane, a hydrocarbyl and/or heterocarbyl silane with a diol at a molar ratio of about 0.1 mole to about 3.0 moles of diol per 1 mole of silyl group to be transesterified. In another embodiment, the ratio can range from about 1.0 to about 2.5 for a trialkoxysilyl group. In yet a further embodiment, the ratio can range from about 1.5 to about 2.0 for a trialkoxysilyl group. In one embodiment, the reaction can be carried out at a temperature ranging from specifically about 0 to about 150° C., more specifically about 25° C. to about 100° C. and most specifically about 60° C. to about 80° C. and all subranges therebetween while maintaining a pressure in the range of from about 0.1 to about 2000 mm Hg absolute. In one embodiment, the temperature can range from about 30° C. to about 90° C. and all subranges therebetween. In another embodiment, the pressure can range from about 1 to about 80 mm Hg absolute. As those skilled in the art will recognize, in one embodiment, excess diol can be utilized to increase reaction rate, but it is not necessary under these conditions as it can increase the cost. In another embodiment, the reaction can be carried out by slowly adding diol to the mixture of the mercaptofunctional alkoxysilane and hydrocarbyl and/or heterocarbyl silane at the desired reaction temperature and vacuum. In another embodiment, as the lower boiling X—H group, such as the mono alcohol, is formed, it can be removed from the reaction mixture by a distillation cycle and removal of the mono alcohol helps drive the reaction to completion. In one embodiment, the reactions optionally can be catalyzed using a transesterification catalyst. In yet a further embodiment, suitable tranesterification catalysts are strong protic acids whose $pK_a$ are below 5.0, transition metal complexes such as complexes of tin, iron, titanium and other metal catalysts. In one embodiment, catalysts suitable for these reaction are disclosed in, "The Siloxane Bond, Physical Properties and Chemical Transformations", M. G. Voronkov, V. P. Mileshkevich and Yu. A. Yuzhelevskii, Consultants Bureau, a division of Plenum Publishing Company, New York (1978), Chapter 5 and is incorporated by reference herein in its entirety. In a further embodiment, strong bases are generally unsuitable as transesterification catalysts since they promote the reaction of the mercaptofunctional group with the diol and result in the formation of sulfides. In one embodiment, the acid or metal catalysts can be used at a range of specifically from about 10 ppm to about 2 weight percent, more specifically from about 20 ppm to about 1000 ppm, and most specifically of from about 100 ppm to about 500 ppm.

In a further embodiment herein, the final mixture can optionally be buffered after the reaction is complete. In one specific embodiment, buffering the mixture will neutralize the strong protic acids and thereby be less corrosive to metals and add to long-term product stability. In a still further specific embodiment, buffering can be conducted through methods and compounds known in the art.

In one specific embodiment, the products of the transesterification of mercaptofunctional and hydrocarbyl and/or heterocarbyl silanes can comprise a considerable fraction of monomeric material in addition to the formation of dimers and other cyclic and/or bridged oligomers as illustrated by low viscosity reaction products. In one specific embodiment the fraction of monomeric material is of from about 1 to about 99 mole percent, more specifically of from about 10 to about 50 mole percent, and most specifically of from about 15 to about 25 mole percent.

In a further embodiment, the process for making the organofunctional silane compositions herein can optionally employ an inert solvent. In a specific embodiment, the solvent can serve as a diluent, carrier, stabilizer, refluxing aid or heating agent. In a more specific embodiment, generally, any inert solvent that does not enter into the reaction or adversely affect the preparative process can be used. In one embodiment, the solvents are liquid under normal conditions and have a boiling point below about 150° C. In a more specific embodiment, some non-limiting examples of suitable solvents include aromatic or aliphatic hydrocarbon, ether, aprotic, or chlorinated hydrocarbon solvents such as toluene, xylene, hexane, butane, diethyl ether, dimethylformamide, dimethyl sulfoxide, carbon tetrachloride, methylene chloride, and combinations thereof.

In one embodiment herein, the process of transesterifying the alkoxysilane with polyhydroxy-containing compound can be conducted continuously. In one more embodiment, in the case of a continuous operation, the process comprises:

a) reacting, in a thin film reactor, a thin film reaction medium comprising a mixture of at least one silane of Formulae (1) or (2) and a mercaptosilane of Formula (3), with at least one polyhydroxy-containing compound of Formula (6) and, optionally, transesterification catalyst, to provide mercapto and hydrocarbyl and/or heterocarbyl functional silanes that contains a cyclic and/or bridged dialkoxy group, and by-product mono alcohol;

b) vaporizing by-product mono alcohol from the thin film to drive the reaction;

c) optionally, recovering by-product mono alcohol by condensation;

d) recovering the organofunctional silane reaction product(s); and, e) optionally, neutralizing the reaction medium to improve the storage stability of the mercapto functional silane product(s) therein.

In one embodiment herein, the molar ratio of polyhydroxy-containing compound to the mixture of mercapto and hydrocarbyl and/or heterocarbyl silanes used in the continuous thin film process will depend upon the number of alkoxy groups that are desired to be replaced with a polyhydroxy-containing group, such as the non-limiting example of a diol (glycol). In one more specific embodiment, theoretically, a molar ratio of about 0.5 mole of diol of Formula (7) or (8) is required per mole of alkoxy-silyl group to be transesterified to replace all of the mono alkoxy or other X-groups. In another embodiment herein, a molar ratio of from about 0.1 to about 1.0 moles of diol can be used per mole of alkoxy-silyl group. In yet another embodiment herein, a molar ratio of from about 0.5 to about 1.0 moles of diol can be used per mole of alkoxy-silyl group. In a further embodiment, and, in many cases, additional diol is desirable because in some cases only one of the hydroxyl groups of the diol reacts with the alkoxysilyl group. In one embodiment these diols that react only once with a silyl group are defined as $X^\alpha$ in Formulae (10) and (11). In a further embodiment, the diols, referred to herein as "hydroxyalkoxy", reduce the viscosity and inhibit the gelation of the silane. In a still further embodiment and as one skilled in the art will readily recognize, excess diol can be utilized to increase reaction rates.

In one specific embodiment, the method of forming the film can be any of those known in the art. In a more specific embodiment, typical known devices include but are not limited to, falling film or wiped film evaporators. In one specific embodiment, minimum film thickness and flow rates will depend on the minimum wetting rate for the film forming surface. In another specific embodiment, maximum film thickness and flow rates will depend on the flooding point for the film and device. In a still further specific embodiment, the alcohol is vaporized from the film by heating the film, by reducing pressure over the film, or by a combination of both. In one embodiment, mild heating and reduced pressure are utilized to form the structures described herein. In yet a further embodiment, optimal temperatures and pressures (partial vacuum) for running the processes described herein will depend upon the specific mercaptofunctional or hydrocarbyl or heterocarbyl silane's alkoxy groups and the diol used in the process. In yet an even further embodiment, additionally if an optional inert solvent is used in the process, that choice will affect the optimal temperatures and pressures (partial vacuum) utilized. In one specific embodiment, some non-limiting examples of such solvents include those listed herein. In one embodiment herein, the by-product X—H, such as a monofunctional alcohol, vaporized from the film is removed from the reactive distillation device by a standard partial vacuum-forming device and can be condensed, collected, and recycled as feed to other processes. In one embodiment, the silane product is recovered by standard means from the reactive distillation device as a liquid phase. In another embodiment, if an inert solvent has been used or if additional purification is necessary, the silane product can be fed to another similar distillation device or distillation column to effect that separation. In still another specific embodiment, optionally the transesterified reaction products can be neutralized to improve product storage.

In another embodiment herein, a process for preparing the mercaptofunctional silanes containing hydrocarbylsilane and/or heterocarbylsilane groups comprises:

a) transesterifying at least one mercaptofunctional silane of chemical structure:

$$(HS)_r\text{—}G^2\text{—}(SiX_3)_s \quad (3)$$

wherein each occurrence of $G^2$, X, r, and s is as defined as herein, and with the proviso that at least one of X is a hydrolyzable group; with a diol or polyhydroxy compound, optionally in the presence of a catalyst;

b) optionally, removing the by-product X—H, such as mono alcohol;

c) tranesterifying the hydrocarbyl and/or heterocarbylsilane or mixture thereof of the chemical structure:

$$G^1\text{—}(SiX_3)_s \quad (1)$$

and/or $$[G^3\text{—}(YG^2)_k Y]_j\text{—}G^2\text{—}(SiX_3)_s \quad (2)$$

wherein each occurrence of $G^1$, $G^2$, $G^3$, Y, X, j, k and s is as defined as herein and with the proviso that at least one of X is a hydrolyzable group with a diol or polyhydroxy compound, optionally in the presence of a catalyst;

d) optionally, removing the by-product X—H, such as mono alcohol;

e) and mixing the compounds from process (a) or (b) with the compounds of process (c) or (d), optionally in a desired ratio; and f) optionally, neutralizing protonic transesterification catalyst, if utilized, with a base.

In one embodiment herein, the amount of hydrocarbyl and/or heterocarbyl silane of chemical structures of Formulae (1) and/or (2):

$$G^3\text{—}(SiX_3)_s \quad (1)$$

$$[G^3\text{—}(YG^2)_k Y]_j\text{—}G^2\text{—}(SiX_3)_s \quad (2)$$

and the amount of mercaptofunctional silane of chemical structure of Formula (3):

$$(HS)_r\text{—}G^2\text{—}(SiX_3)_s \quad (3)$$

wherein each occurrence of $G^1$, $G^2$, $G^3$, Y, X, j, k, r, and s is as defined as herein and with the proviso that at least one of the X is a hydrolyzable group, are mixed in a molar ratio of silanes of Formula (1) and/or (2) to silane Formula (3) in a range of specifically from about 20:1 to about 0.05:1, more specifically from about 5:1 to about 0.2:1, and most specifically from about 2:1 to about 0.5:1.

In one more specific embodiment, if a protic catalyst is used to promote the transesterification of the silanes with diol, it can be useful to neutralize the catalyst with a base to improve the product's stability; however, only a stoichiometric amount of base is required to neutralize the protic catalyst; larger amounts of base will promote undesirable side reactions.

In one specific embodiment, it is understood that the desired ratio of mercapto groups to the hydrocarbyl and/or heterocarbyl groups is determine by the mix ratio. In another specific embodiment, the structure of the silane prepared can be bimodal in distribution. In yet a further specific embodiment, the oligomers and polymers formed can have segments where the nearest neighbors of the mercapto group are other mercapto groups and likewise the nearest neighbors of the hydrocarbyl and/or heterocarbyl group are other hydrocarbyl and/or heterocarbyl groups. In one embodiment, the distribution of mercapto and hydrocarbyl and/or heterocarbyl groups is therefore not random.

Further in another embodiment, a free flowing filler composition is provided which comprises:

a) at least one particulate filler; and, b) a mercaptofunctional silane composition comprising at least one organofunctional silane selected from the group consisting of:

(i) mercaptosilane possessing at least one hydroxyalkoxysilyl group and/or a cyclic dialkoxysilyl group, (ii) hydrocarbyl and/or heterocarbyl silane possessing at least one hydroxyalkoxysilyl group and/or a cyclic dialkoxysilyl group, (iii) mercaptosilane dimer in which the silicon atoms of the mercaptosilane units are bonded to each other through a bridging dialkoxy group, each silane unit optionally possessing at least one hydroxyalkoxysilyl group and/or a cyclic dialkoxysilyl group, (iv) hydrocarbyl and/or heterocarbyl silane dimer in which the silicon atoms of the hydrocarbyl and/or heterocarbyl silane units are bonded to each other through a bridging dialkoxy group, each silane unit optionally possessing at least one hydroxyalkoxysilyl group and/or a cyclic dialkoxysilyl group, (v) silane dimer possessing a mercaptosilane unit the silicon atom of which is bonded to the silicon atom of a hydrocarbyl and/or heterocarbyl silane unit through a bridging dialkoxy group, each silane unit optionally possessing at least one hydroxyalkoxysilyl group and/or a cyclic dialkoxysilyl group, (vi) mercaptosilane oligomer in which the silicon atoms of adjacent mercaptosilane units are bonded to each other through a bridging dialkoxy group, the terminal mercaptosilane units possessing at least one hydroxyalkoxysilyl group and/or a cyclic dialkoxysilyl group, (vii) hydrocarbyl and/or heterocarbyl silane oligomer in which the silicon atoms of adjacent hydrocarbyl and/or heterocarbyl silane units are bonded to each other through a bridging dialkoxy group, the terminal mercaptosilane units possessing at least one hydroxyalkoxysilyl group and/or a cyclic dialkoxysilyl group, and (viii) silane oligomer possessing at least one mercaptosilane unit and at least one hydrocarbyl and/or heterocarbyl silane unit, the silicon atoms of adjacent silane units being bonded to each other through a bridging dialkoxy group, the terminal silane units possessing at least one hydroxyalkoxysilyl group and/or a cyclic dialkoxysilyl group, with the provisio that, where the composition contains one or more of (i), (iii) and (vi), the composition additionally contains one or more of (ii), (iv), (v), (vii) and (viii), and where the composition contains one or more of (ii), (iv) and (vii), the composition additionally contains one or more of (i), (iii), (v), (vi) and (viii). In one embodiment herein, the filler is reactive with the mercaptofunctional silane composition. In one other embodiment herein, free flowing filler composition can further comprise an elastomer such as any of the elastomeric resins or organic polymers described herein and in the amounts described herein.

In one embodiment of the foregoing free flowing filler composition, mercaptofunctional silane composition comprises at least one of:

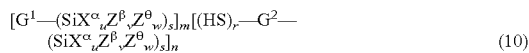

and

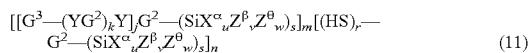

wherein:

each occurrence of Y is independently selected from a polyvalent species $(-Q)_a[C(=E)]_b(A-)_c$, wherein the atom (E) is attached to an unsaturated carbon atom;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms;

each occurrence of $G^1$ is independently selected from the group consisting of divalent or polyvalent group derived by substitution of alkyl, alkenyl, aryl, or aralkyl wherein $G^2$ can have from 1 to 30 carbon atoms;

each occurrence of $G^3$ is independently selected from the group consisting of monovalent and polyvalent groups derived by substitution of alkyl, alkenyl, aryl, or aralkyl wherein $G^3$ can have from 1 to about 30 carbon atoms, with the proviso that if $G^3$ is monovalent, $G^3$ can be hydrogen;

each occurrence of $X^\alpha$ is independently selected from the group consisting of —Cl, —Br, RO—, RC(=O)O—, $R_2C=NO—$, $R_2NO—$, $R_2N—$, —R, $(HO)_{d-1}G^4O—$, $HO(CR^0_2)_fO—$, and $HO(CR^0_2CR^0_2O)_e—$ wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^4$ is independently a substituted hydrocarbon group of from about 2 to about 15 carbon atoms or a substituted heterocarbon group of from about 4 to 15 carbon atoms and contains one or more etheric oxygen atoms, $R^0$ is independently given by one of the members listed for R, f is from about 2 to about 15, and e is from about 2 to about 7;

each occurrence of Q is independently selected from the group consisting of oxygen, sulfur, and (—NR—) and with the proviso that when Q is sulfur, b is 0;

each occurrence of A is independently selected from the group consisting of oxygen, sulfur, and (—NR—) and with the proviso that when A is sulfur, b is 0;

each occurrence of E is independently selected from the group consisting of oxygen, sulfur, and (—NR—);

each occurrence of $Z^\beta$, which forms a bridging structure between two silicon atoms, is independently selected from the group consisting of, $[-OG^4(OH)_{d-2}O-]_{0.5}$, $[-O(CR^0_2CR^0_2O)_e-]_{0.5}$ and $[-O(R^0CR^0)_fO-]_{0.5}$, wherein each occurrence of $R^0$ is independently given by one of the members listed above for R; and, each occurrence of $G^4$ is independently selected form the group consisting of a substituted hydrocarbon group from 2 to 15 carbon atoms or a substituted hetercarbon from 4 to 15 carbon atoms and contain one or more etheric oxygen atoms;

each occurrence of $Z^\theta$, which forms a cyclic structure with a silicon atom, is independently given by $-OG^4(OH)_{d-2}O-$, $-O(CR^0_2CR^0_2O)_n-$ and $-O(R^0CR^0)_fO-$ wherein each occurrence of $R^0$ is independently given by one of the members listed above for R;

each occurrence of the subscripts, a, b, c, d, e, f, j, k, m, n, r, s, u, v, and w are integers independently given by a is specifically 0 or 1, and more specifically 1; b is specifically 0 or 1, and more specifically 0; c is specifically 0 or 1, and more specifically 0; d is specifically from about 2 to about 8, more specifically from about 2 to about 4 and most specifically about 2; e is specifically from about 2 to about 7, more specifically from about 2 to about 4 and most specifically about 2; f is specifically from about 2 to about 15, more specifically from about 2 to about 4 and most specifically about 3; j is specifically from 1 to about 3, more specifically from about 1 to about 2, and most specifically about 1; k is specifically from 0 to about 15, more specifically from about 0 to about 5, and most specifically from about 0 to about 2; m is specifically from about 1 to about 20, more specifically from about 1 to about 5 and most specifically from about 2 to 4; n is specifically from about 1 to about 20, more specifically from about 1 to about 5 and most specifically from about 2 to about 4; r is specifically from 1 to about 3, and more specifically about 1; and s is specifically from 1 to about 3, more specifically about 1; u is specifically from 0 to 3, more specifically from about 0 to about 2, and most specifically from about 0 to about 1; v is specifically from 0 to 3, more specifically from about 0 to about 2, and most specifically from about 0 to about 1; w is specifically from 0 to about 1, and more specifically about 1; with the proviso that u+v+2w=3; and with the proviso that the each of the above structures (10) and/or (11) contains at least one hydrolysable group, $Z^\beta$ or $Z^\theta$. In one embodiment, it is understood that the structure, $[-OG^4(OH)_{d-2}O-]_{0.5}$ can further react with a third or more silyl groups to form bridging trialkoxysilyl, tetraalkoxysilyl groups and so on, and are represented by $[-OG^4(OH)_{d-3}(O-)_2]_{1/3}$, $[-OG^4(OH)_{d-4}(O-)_3]_{1/4}$ and so on, respectively.

In another embodiment herein there is provided an article of manufacture, such as the non-limiting examples selected from the group consisting of tires, industrial goods, shoe soles, hoses, seals, gaskets, and cable jackets, of which at least one component is the cured rubber composition of the herein described rubber compositions. In one embodiment, the silanes and/or silane mixtures herein offer a means for significantly reducing volatile organic compound (VOC) emissions during rubber manufacture, increase the dispersion of the filler within the rubber, and improving the coupling between the organic polymers and fillers.

In another embodiment herein the organofunctional silane-based compositions described herein are useful as coupling agents between elastomeric resins (i.e., rubbers) and fillers. In one embodiment, the organofunctional silane compositions are unique in that the high efficiency of the mercaptan group can be utilized without the detrimental side effects typically associated with the use of mercaptosilanes, such as high processing viscosity, less than desirable filler dispersion, premature curing (scorch), and odor. In yet another embodiment, these benefits are obtained because the mercaptan group is part of a high boiling compound that liberates diol or higher polyhydroxy-containing compound upon use. In yet still another embodiment, the combination of mercapto and hydrocarbyl and/or heterocarbyl groups in this silane-based composition allow for a controlled amount filler dispersion during the preparation of the free flowing filler composition and of coupling to the organic polymer during the compounding of the rubber. In yet still even another embodiment, during this non-productive mixing step, the cyclic and/or bridged alkoxysilyl groups can react with the filler. In one embodiment herein mercaptosilane composition, free-flowing filler composition and rubber composition can be cured as described herein and/or using procedures known to those skilled in the art.

In another specific embodiment herein, the mercaptofunctional silane-based compositions herein provide significant advantages over traditional coupling agents that have found extensive use in the rubber and tire industries. These traditional silanes usually contain in their molecular structures three alkoxy groups, e.g., ethoxy groups, on each silicon atom, which results in the release of up to three moles of simple monohydroxy alcohol, e.g., ethanol for each silane equivalent during the rubber manufacturing process in which the silane couples to the filler. The release of simple mono alcohols is a great disadvantage because they are flammable and therefore pose a threat of fire, and because they contribute so greatly to volatile organic compound (VOC) emissions and are therefore potentially harmful to the environment.

In one specific embodiment herein, utilizing any of the silanes and/or silane mixtures disclosed herein can result in VOC emission that is reduced. In one embodiment, VOC emission from a product/composition comprising the silanes or silanes mixtures disclosed herein can be less than the VOC emission in an equivalent product/composition that does not contain said silanes or silanes mixtures disclosed herein. In yet a further embodiment, reduced VOC emission can comprise specifically less than about 30 weight percent of the weight of the mercaptofunctional silane, more specifically less than about 10 weight percent of the mercaptofunctional silane and most specifically less than about 1 weight percent of the mercaptofunctional silane. In one embodiment, a VOC emission is defined as at least one selected from the group consisting of $X^\alpha$—H, $G(OH)_d$, $(HO)(CR^0{}_2)_fOH$ and $HO(CR^0{}_2CR^0{}_2O)_eOH$, all having a boiling point greater than 180° C. at atmospheric pressure.

In one embodiment herein, the organofunctional silane-based compositions described herein eliminate or greatly mitigate the foregoing problems by reducing volatile mono alcohol emissions to only one, less than one, and even essentially zero, moles of mono alcohol per silane equivalent. In one specific embodiment, they accomplish this because the silane alkoxy groups are replaced with polyhydroxy alcohols, e.g., diol derived bridging groups, and thus such polyhydroxy alcohols are released during the rubber manufacture process in place of much, or nearly all, of the mono alcohol released. In yet a further specific embodiment, describing the advantages of the organofunctional silanes herein with specific reference to those silanes that are prepared with diols (such advantages being realizable with polyhydroxy-containing compounds of higher hydroxyl functionality), e.g., having boiling points in excess of rubber processing temperatures, are not vaporized out of the rubber during the rubber manufacture process, as is the case, e.g., with ethanol, but are retained by the rubber where they migrate to the silica surface due to their high polarity and become hydrogen bonded to the surfaces of siliceous fillers such as silicas. In another embodiment, the presence of diols on silica surfaces leads to further advantages not obtainable with ethanol (due to its volatility and ejection during the rubber compounding process) in the subsequent cure process, in which such presence prevents the silica surface from binding the curatives and thereby interfering with the cure. Traditional silanes not based on diols require more curatives to counter losses due to silica binding.

In another embodiment, the addition of hydrocarbon-based diols or polyhydroxyl-containing compounds to the rubber compounding formulation prior to and/or concurrent with the addition of curatives is of advantage for the efficient utilization of the curatives, in particular, and polar substances, such as, but not limited to, amines, amides, sulfenamides, thiurams, and guanidines. In yet another embodiment, whether diols or the polyhydroxyl-containing compounds are exclusively added in the form of di- or polyhydroxyl-derived silanes or as free diols or polyhydroxyl-containing compounds in combination with the silane coupling agents, the polarity of the diols or polyhydroxyl-containing compounds is of advantage to the rubber compounding process. In one more embodiment, these polar substances tend to migrate to the filler surface due to dipole interactions with the filler; which tends to make them unavailable within the organic polymer matrix, where their functions include dispersion of the free flowing filler composition and acceleration, or retardation, of the curing reactions. In one embodiment, the hydrocarbon-based diols or polyhydroxyl-containing compounds enhance the function of the curatives by interfering with their tendency to bind to the silica surface thereby forcing them into the rubber matrix to perform their function. In another embodiment herein, the hydrocarbon-based diols or polyhydroxyl-containing compounds accomplish this by themselves being very polar, and thereby by themselves binding to the filler surface, leaving less room for the curatives to bind to filler. In a further specific embodiment, the hydrocarbon-based diols thus act as curative displacing agents from the filler. In yet another specific embodiment, the short chain of the hydrocarbon-based diols or polyhydroxyl-containing compounds further enhances their function by a chelate effect. In one embodiment, the number of carbon atoms between the dialkoxide groups of $Z^\theta$ and/or $Z^\beta$ herein are important and are defined by the divalent radical —O($R^0CR^0$)$_f$O— and [—O($R^0CR^0$)$_f$O—]$_{0.5}$, respectively, wherein each occurrence of f is 2 or 3. In a more specific embodiment, these chains of two or three carbon atoms between the two OH groups of the diol promote the formation of 5- or 6-membered rings when both oxygen atoms bind to a common silicon atom of the silanes of Formulae (10) and (11). In an even more specific embodiment, this dual binding to a common center, known, and referred to herein as the chelate effect, increases the amount of cyclic dialkoxysilyl group and inhibits the formation of gel. In a further specific embodiment, after reactions with the silica in the rubber-compounding step, the diols that have been released have a high affinity to the filler because they can chelate with the metal or silicon atom on the filler surface thereby enhancing their ability to prevent the binding of the curatives to the filler. In a further specific embodiment an important advantage of the silanes and/or silane mixtures described herein is that the by-products of the silane coupling process are themselves of utility in enhancing the rubber compounding process, the value of the resulting rubber compositions, and/or any articles of manufacture employing the rubber compositions. In one embodiment, thus, the hydrocarbyl and/or heterocarbyl groups of the silanes and/or silane mixtures ("silanes") not only retards coupling of silane to polymer during mixing but also assists in the dispersion of the filler into the polymer during mixing by reducing the ability of the surface hydroxyl or metal oxides to form hydrogen bonds between filler particles, thereby enhancing the ease and completeness of filler dispersion and retarding the reversal of this process, namely, filler reagglomeration.

In one embodiment herein there is provided a rubber composition comprising (a) at least one rubber component, (b) at least one particulate filler and (c) at least one mercaptofunctional silane or mercaptofunctional silane composition as described herein. In one embodiment herein rubber composition can have any of the embodiments discussed herein for free-flowing filler composition, mercaptosilane composition and process of making mercaptosilane and vice-versa.

In one embodiment, an important advantage of the silanes described herein is that the by-products of the silane coupling process are themselves of utility in enhancing the rubber compounding process, the value of the resulting rubber compositions, and/or any articles of manufacture employing the rubber compositions. In another embodiment, thus, the hydrocarbyl and/or heterocarbyl groups of the silanes herein not only retards coupling of silane(s) to polymer during mixing but also assists in the dispersion of the filler into the polymer during mixing by reducing the ability of the surface hydroxyl or metal oxides to form hydrogen bonds between filler particles, thereby enhancing the ease and completeness of filler dispersion and retarding the reversal of this process, namely, filler reagglomeration.

In one embodiment, at least one of the organofunctional silane coupling agents that contain cyclic and/or bridging dialkoxysilyl groups and mercapto and hydrocarbyl and/or heterocarbyl groups is mixed with the organic polymer before, during, or after the compounding of the filler into the organic polymer. In one embodiment, the silanes are added before or during the compounding of the filler into the organic polymer because these silanes facilitate and improve the dispersion of the filler. In a more specific embodiment, the total amount of silane present in the resulting rubber composition should be about 0.05 to about 25 parts by weight per hundred parts by weight of organic polymer (phr). In another embodiment, the amount of mercaptofunctional silane present in the free flowing filler composition is from about 0.1 to about 70 weight percent based on total weight of free flowing filler composition. In yet another embodiment, the amount of mercaptofunctional silane present in the free flowing filler composition is from about 0.5 to about 20 weight percent based on total weight of free flowing filler composition. In one other embodiment the amount of filler in the free flowing filler composition is from about 99.9 to about 30 weight percent based on total weight of free flowing filler composition. In yet one other embodiment the amount of filler in the free flowing filler composition is from about 99.5 to about 80 weight percent based on total weight of free flowing filler composition. In another embodiment, the amount of silane present in the rubber is from about 1 to 10 phr. In yet another embodiment, the amount of silane present in the rubber is from about 3 to 8 phr. In one embodiment, fillers can be used in quantities ranging specifically from about 5 to about 100 phr, more specifically from about 25 to about 80 phr and most specifically from about 50 to about 70 phr.

In one embodiment, in practice, sulfur vulcanized rubber products typically are prepared by thermomechanically mixing rubber and various ingredients in a sequentially step-wise manner followed by shaping and curing the compounded rubber to form a vulcanized product. In a more specific embodiment, first, for the aforesaid mixing of the rubber and various ingredients, typically exclusive of sulfur and sulfur vulcanization accelerators (collectively "curing agents"), the rubber(s) and various rubber compounding ingredients are usually blended in at least one, and optionally (in the case of silica filled low rolling resistance tires) two or more, preparatory thermomechanical mixing stage(s) in suitable mixers. In a further embodiment, such preparatory mixing is referred to as non-productive mixing or non-productive mixing steps or stages. In a more specific embodiment, such preparatory mixing usually is conducted at temperatures in the range of from about 140° C. to about 200° C. and often in the range of from about 150° C. to about 180° C.

In one embodiment, subsequent to such preparatory mix stages, in a final mixing stage, sometimes referred to as a productive mix stage, curing agents, and possibly one or more additional ingredients, are mixed with the rubber compound or composition, typically at a temperature in a range of 50° C. to 130° C., which is a lower temperature than those utilized in the preparatory mix stages to prevent or retard premature curing of the sulfur curable rubber, which is sometimes referred to as scorching of the rubber composition.

In another embodiment, the rubber mixture, sometimes referred to as a rubber compound or composition, typically is allowed to cool, sometimes after or during a process of intermediate mill mixing, between the aforesaid various mixing steps, for example, to a temperature of about 50° C. or lower.

In another embodiment herein, when it is desired to mold and to cure the rubber, the rubber is placed into the appropriate mold and heated to about at least 130° C. and up to about 200° C., which will cause the vulcanization of the rubber by the mercapto groups on the mercaptosilane and any other free sulfur sources in the rubber mixture.

In one embodiment, by thermomechanical mixing, it is meant that the rubber compound, or composition of rubber and rubber compounding ingredients, is mixed in a rubber mixture under high shear conditions where it autogenously heats up as a result of the mixing, primarily due to shear and associated friction within the rubber mixture in the rubber mixer. In one embodiment, several chemical reactions can occur at various steps in the mixing and curing processes.

In one embodiment, the first reaction is a relatively fast reaction and is considered herein to take place between the filler and the alkoxysilyl group of the cyclic and/or bridging dialkoxy blocked mercaptofunctional silanes, —SiX$^{\alpha}_{u}$Z$^{\beta}_{v}$Z$^{\theta}_{w}$, herein. In a further embodiment, such reaction can occur at a relatively low temperature, such as, for example, about 120° C. In a further embodiment, the second reaction is considered herein to be the reaction which takes place between the sulfur-containing portion of the silane, and the sulfur vulcanizable rubber at a higher temperature; for example, above about 140° C.

In one embodiment, another sulfur source can be used, for example, in the form of elemental sulfur as S$_8$. In a more specific embodiment, a sulfur donor is considered herein as a sulfur-containing compound that liberates free, or elemental sulfur, at a temperature in a range of about 140° C. to about 190° C. In an even more specific embodiment, such sulfur donors can be those such as the non-limiting examples of polysulfide vulcanization accelerators with at least two connecting sulfur atoms in their polysulfide bridge. In an even yet more specific embodiment, the amount of free sulfur source addition to the mixture can be controlled or manipulated as a matter of choice relatively independently from the addition of the aforesaid cyclic and/or bridging dialkoxy mercaptofunctional silane composition.

Thus, in one embodiment for example, the independent addition of a sulfur source can be manipulated by the amount of addition thereof and by sequence of addition relative to addition of other ingredients to the rubber mixture.

In another embodiment herein, a rubber composition is prepared by a process comprising the sequential steps of:
(a) thermomechanically mixing, in at least one preparatory mixing step, to a temperature of 140° C. to 200° C., alternatively to 140° C. to 180° C., for a total mixing time of 2 to 20, alternatively 4 to 15, minutes for such mixing step(s):
  i) 100 parts by weight of at least one sulfur vulcanizable rubber selected from conjugated diene homopolymers and copolymers, and copolymers of at least one conjugated diene and aromatic vinyl compound,
  ii) 5 to 100, preferably 25 to 80, phr of particulate filler, wherein the filler preferably contains from 1 to 85 weight percent carbon black, and
  iii) 0.05 to 20 parts by weight filler of at least one mercaptofunctional cyclic and/or bridging dialkoxy silane of the composition described herein;
(b) subsequently blending therewith, in a final thermomechanical mixing step at a temperature to 50° C. to 130° C. for a time sufficient to blend the rubber, specifically between 1 to 30 minutes, more specifically 1 to 3 minutes, and a curing agent at 0 to 5 phr; and, optionally; and,
(c) curing said mixture at a temperature in the range of from 130 to 200° C. for about 5 to 60 minutes.

In one embodiment, suitable rubber component (a) (organic polymers) and fillers are well known in the art and are described in numerous texts, of which two examples include The Vanderbilt Rubber Handbook; R. F. Ohm, ed.; R.T. Vanderbilt Company, Inc., Norwalk, Conn.; 1990 and Manual For The Rubber Industry; T. Kempermann, S. Koch, J. Sumner, eds.; Bayer AG, Leverkusen, Germany; 1993. In yet an even further embodiment, some representative non-limiting examples of suitable rubber component (a) (organic polymers) include solution styrene-butadiene rubber (SSBR), emulsion styrene-butadiene rubber (ESBR), natural rubber (NR), polybutadiene (BR), ethylene-propylene terpolymers (EPDM), and acrylonitrile-butadiene rubber (NBR).

In another embodiment herein, the rubber composition component (a) is comprised of at least one diene-based elastomer, or rubber. In an even more specific embodiment, suitable monomers for preparing the rubbers are conjugated dienes which are those such as the non-limiting examples of isoprene and 1,3-butadiene; and suitable vinyl aromatic compounds which are those such as the non-limiting examples of styrene and alpha methyl styrene; and combinations thereof. Thus in a more specific embodiment, the rubber is a sulfur curable rubber. In a further embodiment, such diene based elastomer, or rubber, can be selected, from the non-limiting examples of at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (ESBR) is also contemplated as diene based rubbers for use herein such as those having a relatively conventional styrene content of 20 to 28 percent bound styrene or, for some applications, an ESBR having a medium to relatively high bound styrene content, namely, a bound styrene content of 30 to 45 percent. In an even further specific embodiment, emulsion polymerization prepared styrene/butadiene/acrylonitrile terpolymer rubbers containing 2 to 40 weight percent bound acrylonitrile in the terpolymer are also contemplated as diene based rubbers for use herein.

In another embodiment herein, the solution polymerization prepared SBR (SSBR) typically has a bound styrene content in a range of specifically from about 5 to about 50, more specifically from about 9 to about 36, and most specifically of from about 20 to about 30 weight percent. In a more specific embodiment, polybutadiene elastomer can be conveniently characterized, for example, by having at least a 90 weight percent cis-1,4-content.

In one embodiment some representative non-limiting examples of suitable filler materials include metal oxides, such as silica (pyrogenic and precipitated), titanium dioxide, aluminosilicate, and alumina, siliceous materials, including clays and talc, and carbon black. In a more specific embodiment, particulate, precipitated silica is also sometimes used for such purpose, particularly in connection with a silane. In one embodiment wherein the filler is a silica alone or in combination with one or more other fillers. In another specific embodiment in some cases, a combination of silica and carbon black is utilized for reinforcing fillers for various rubber products, including treads for tires. In one embodiment, alumina can be used either alone or in combination with silica. The term "alumina" can be described herein as aluminum oxide, or $Al_2O_3$. In a further specific embodiment, the fillers can be hydrated or in anhydrous form. Use of alumina in rubber compositions is known, see, for example, U.S. Pat. No. 5,116,886 and EP 631 982, the contents of which are incorporated by reference herein.

In one embodiment there is provided herein a process for preparing a rubber composition comprising adding to a rubber composition reaction-forming mixture, such as a mixture of the herein described rubber composition components (a), (b) and (c) in an effective amount of at least one mercaptofunctional silane composition as described herein. In one embodiment an effective amount of mercaptofunctional silane composition, in a rubber composition reaction forming mixture, as described herein, is specifically of from about 1 to about 20, more specifically of from about 3 to about 15 and most specifically of from about 5 to about 10 weight percent of mercaptofunctional silane based on the total weight of rubber composition reaction forming mixture. In another embodiment, reaction-forming mixture further comprises a filler as described herein and in an amount of specifically of from about 2 to about 70, more specifically of from about 5 to about 50 and most specifically of from about 20 to about 40 weight percent of filler, based on the total weight of rubber composition reaction forming mixture. In yet another embodiment reaction-forming mixture can even further comprise a rubber component (a) described herein, and in an amount of specifically of from about 30 to about 98, more specifically of from about 50 to about 95 and most specifically of from about 60 to about 80 weight percent of rubber component based on the total weight of rubber composition reaction forming mixture. In one embodiment herein, rubber composition as described herein can have amounts of components (a), (b) and (c) as described for rubber component reaction forming mixture.

In one embodiment, the organofunctional silane compositions that contain cyclic and/or bridging dialkoxysilyl groups and mercapto and heterocarbyl and/or hydrocarbyl groups can be premixed, or pre-reacted, with the filler particles or added to the rubber mix during the rubber and filler processing, or mixing stage. In another embodiment, if the silane and filler are added separately to the rubber mix during the rubber and filler mixing, or processing stage, it is considered that the organofunctional silane compositions that contain cyclic and/or bridging dialkoxysilyl groups and mercapto and heterocarbyl and/or hydrocarbyl groups then couple in situ to the filler.

In one embodiment herein, vulcanized rubber composition should contain a sufficient amount of filler to contribute a reasonably high modulus and high resistance to tear. In a specific embodiment, the combined weight of the filler can be as low as about 5 to about 100 phr, but is more specifically of from about 25 to about 85 phr, and most specifically of from about 50 to about 70 phr.

In one embodiment the term "filler" as used herein means a substance that is added to the elastomer to either extend the elastomer or to reinforce the elastomeric network. Reinforcing fillers are materials whose moduli are higher than the organic polymer of the elastomeric composition and are capable of absorbing stress from the organic polymer when the elastomer is strained. In one embodiment fillers included fibers, particulates, and sheet-like structures and can be composed of inorganic minerals, silicates, silica, clays, ceramics, carbon, organic polymers, diatomaceous earth. In one embodiment the filler herein can be essentially inert to the silane with which it is admixed, or it can be reactive therewith.

In one embodiment the term "particulate filler" as used herein means a particle or grouping of particles to form aggregates or agglomerates. In one embodiment the particulate filler herein can be essentially inert to the silane with which it is admixed, or it can be reactive therewith.

In one embodiment the term "carrier" as used herein means a porous or high surface area filler that has a high adsorption or absorption capability and is capable of carrying up to 75 percent liquid silane while maintaining its free-flowing and dry properties. In one embodiment the carrier filler herein is essentially inert to the silane and is capable of releasing or deabsorbing the liquid silane when added to the elastomeric composition.

In an embodiment, fillers of the present invention can be used as carriers for liquid silanes and reinforcing fillers for elastomers in which the mercapto functional silane, and more specifically, the mercaptofunctional silane (10) or (11) is capable of reacting or bonding with the surface. In one embodiment, the fillers that are used as carrier should be non-reactive with the with the mercaptosilane of this invention. In one embodiment the non-reactive nature of the fillers is demonstrated by ability of the merpcaptosilane to be extracted at greater than 50 percent of the loaded silane using an organic solvent. In one embodiment the extraction procedure is given in U.S. Pat. No. 6,005,027, which is incorporated herein by reference. In one embodiment, carriers include, but are not limited to, porous organic polymers, carbon black, diatomaceous earth, and silicas that characterized by relatively low differential of less than 1.3 between the infrared absorbance at 3502 $cm^{-2}$ of the silica when taken at 105° C. and when taken at 500° C., as described in U.S. Pat. No. 6,005,027. In one embodiment, the amount of mercapto functional silane that can be loaded on the carrier is between 0.1 and 70 percent. In another embodiment, the mercpato functional silane is load on the carrier at concentrations between 10 and 50 percent. In yet another embodiment, the filler is a particulate filler.

In one embodiment herein reinforcing fillers useful herein include fillers in which the silanes are reactive with the surface of the filler. In one embodiment some representative examples of the fillers include, but are not limited to, inorganic fillers, siliceous fillers, metal oxides such as silica (pyrogenic and/or precipitated), titanium, aluminosilicate and alumina, clays and talc, and the like. In one embodiment herein, particulate, precipitated silica is useful for such purpose, particularly when the silica has reactive surface silanols. In one embodiment of the present invention, a combination of 0.1 to 20 percent of mercapto functional silane, and more specifically, the mercapto functional silanes (10) or (11) and 80 to 99.9 percent silica or other reinforcing fillers is utilized to reinforce various rubber products, including treads for tires. In another embodiment, a filler is comprising from about 0.5 to about 10 percent mercapto-functional silane, and more specifically, mercapto functional silane (10) or (11) and about 90 to about 99.5 weight percent particulate filler. In another embodiment herein, alumina can be used alone with the mercapto functional silane, and more specifically, mercaptofunctional silane (10) or (11) or in combination with silica and the mercapto functional silane. In one embodiment herein the term, alumina, can be described herein as aluminum oxide, or $Al_2O_3$. In a further embodiment herein, the fillers may be in the hydrated form.

In one embodiment the filler can be essentially inert to the silane with which it is admixed as is the case with carbon black or organic polymers, or it can be reactive therewith, e.g., the case with carriers possessing metal hydroxyl surface functionality, e.g., silicas and other siliceous particulates which possess surface silanol functionality.

In one embodiment herein, precipitated silica is utilized as filler. In a more specific embodiment, the silica filler herein can as characterized by having a BET surface area, as measured using nitrogen gas, specifically in the range of from about 40 to about 600 $m^2/g$, and more specifically in a range of from about 50 to about 300 $m^2/g$ and most specifically in a range of from about 100 to about 150 $m^2/g$. In another specific embodiment, the BET method of measuring surface area is described in the Journal of the American Chemical Society, Volume 60, page 304 (1930), which is the method used herein. In yet another specific embodiment, the silica typically can also be characterized by having a dibutylphthalate (DBP) absorption value in a range of specifically from about 100 to about 350, more specifically from about 150 to about 300 and most specifically from about 200 to about 250. In an even further specific embodiment, further, useful silica fillers, as well as the aforesaid alumina and aluminosilicate fillers, can be expected to have a CTAB surface area in a range of from about 100 to about 220 $m^2/g$. In an even further specific embodiment, the CTAB surface area is the external surface area as evaluated by cetyl trimethylammonium bromide with a pH of 9; the method is described in ASTM D 3849.

In one embodiment, mercury porosity surface area is the specific surface area determined by mercury porosimetry. In this technique, mercury is penetrated into the pores of the sample after a thermal treatment to remove volatiles. In a more specific embodiment, set-up conditions can be suitably described as using a 100 mg sample; removing volatiles during 2 hours at 105° C. and ambient atmospheric pressure; and ambient to 2000 bars pressure measuring range. In another more specific embodiment, such evaluation can be performed according to the method described in Winslow, et al. in ASTM bulletin, p. 39 (1959) or according to DIN 66133; for such an evaluation, a CARLO-ERBA Porosimeter 2000 can be used. In one embodiment, the average mercury porosity specific surface area for the selected silica filler should be in a range of specifically from about 100 to about 300 $m^2/g$, more specifically from about 150 to about 275 $m^2/g$, and most specifically from about 200 to about 250 $m^2/g$.

In one embodiment, a suitable pore size distribution for the silica, alumina and aluminosilicate according to such mercury porosity evaluation is considered herein to be: five percent or less of its pores having a diameter of less than about 10 nm; from about 60 to about 90 percent of its pores have a diameter of from about 10 to about 100 nm; from 10 to about 30 percent of its pores having a diameter of from about 100 to about 1,000 nm; and from about 5 to about 20 percent of its pores have a diameter of greater than about 1,000 nm. In a second embodiment, the silica can be expected to have an average ultimate particle size, for example, in the range of from about 0.01 to about 0.05 μm as determined by electron microscopy, although the silica particles can be even smaller, or possibly larger, in size. In one embodiment, various commercially available silicas can be considered for use herein such as, those available from PPG Industries under the HI-SIL trademark, in particular, HI-SIL 210, and 243; silicas available from Rhone-Poulenc, e.g., ZEOSIL 1165 MP; silicas available from Degussa, e.g., VN2 and VN3, etc. and silicas available from Huber, e.g., HUBERSIL 8745.

In one embodiment, where it is desired for rubber composition, which contains both a siliceous filler such as silica, alumina and/or aluminosilicates and also carbon black reinforcing pigments, to be primarily reinforced with silica as the reinforcing pigment, it is often more specific that the weight ratio of such siliceous fillers to carbon black is at least 3/1 and preferably at least 10/1 and, thus, in a range of 3/1 to 30/1. In a more specific embodiment, the filler can comprise from about 15 to about 95 weight percent precipitated silica, alumina and/or aluminosilicate and, correspondingly from about 5 to about 85 weight percent carbon black, wherein the said carbon black has a CTAB value in a range of from about 80 to about 150. In one specific embodiment, alternatively, the filler can comprise from about 60 to about 95 weight percent of said silica, alumina and/or aluminosilicate and, correspondingly, from about 40 to about 5 weight percent of carbon black. In another specific embodiment, the siliceous filler and carbon black can be preblended or blended together in the manufacture of the vulcanized rubber.

In one embodiment, the rubber composition herein can be compounded by methods known in the rubber compounding art, such as mixing the various sulfur-vulcanizable constituent rubbers with various commonly used additive materials as, for example, curing aids such as sulfur, activators, retarders and accelerators, processing additives such as oils, resins e.g., tackifying resins, silicas, plasticizers, fillers, pigments, fatty acid, zinc oxide, waxes, antioxidants and antiozonants, peptizing agents, and reinforcing materials such as, for example, carbon black, and the like. In another specific embodiment, depending on the intended use of the sulfur vulcanizable and sulfur vulcanized material (rubbers), the additives mentioned herein are selected and commonly used in conventional amounts.

In one embodiment, the vulcanization can be conducted in the presence of an additional sulfur vulcanizing agent. In one specific embodiment, some non-limiting examples of suitable sulfur vulcanizing agents include, e.g., elemental sulfur (free sulfur) or sulfur donating vulcanizing agents, such as the non-limiting examples of, an amino disulfide, polymeric polysulfide or sulfur olefin adducts, which are conventionally added in the final, productive, rubber composition mixing step. In another specific embodiment, the sulfur vulcanizing agents (which are common in the art) are used, or added in the productive mixing stage, in an amount ranging from about 0.4 to about 3 phr, or even, in some circumstances, up to about 8 phr, with a range of from about 1.5 to about 2.5 phr, and in some cases from about 2 to about 2.5 phr, being most specific.

In one embodiment, vulcanization accelerators, i.e., additional sulfur donors, can also be used. In one embodiment, it will be appreciated that they can be those such as the non-limiting examples of benzothiazole, alkyl thiuram disulfide, guanidine derivatives, and thiocarbamates. In another specific example, representative of such accelerators are, e.g., but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine), dithiobis(dibenzyl amine) and combinations thereof. In another specific embodiment, other additional sulfur donors, include, e.g., thiuram and morpholine derivatives. In a more specific embodiment, representative of such donors include, e.g., but are not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, disulfidecaprolactam and combinations thereof.

In one embodiment, accelerators are used to control the time and/or temperature required for vulcanization and to improve the properties of the vulcanizate. In one embodiment, a single accelerator system can be used, i.e., a primary accelerator. In another embodiment, conventionally and more specifically, a primary accelerator(s) is used in total amounts ranging from about 0.5 to about 4, preferably from about 0.8 to about 1.5, phr. In a more specific embodiment, combinations of a primary and a secondary accelerator can be used with the secondary accelerator being used in smaller amounts (e.g., from about 0.05 to about 3 phr) in order to activate and to improve the properties of the vulcanizate. In yet a further embodiment, delayed action accelerators can also be used. In yet an even further embodiment, vulcanization retarders can also be used. In one embodiment, suitable types of accelerators are those such as the non-limiting examples of amines, disulfides, guanidines, thioureas, thiazoles, thiurams, sulfenamides, dithiocarbamates, xanthates and combinations thereof. In a more specific embodiment, the primary accelerator is a sulfenamide. In another specific embodiment, if a second accelerator is used, the secondary accelerator is more specifically a guanidine, dithiocarbamate or thiuram compound. In one embodiment some non-limiting amounts of tackifier resins, if used, can be from about 0.5 to about 10 phr, usually from about 1 to about 5 phr. In one specific embodiment, typical amounts of processing aids comprise from about 1 to about 50 phr. In another specific embodiment, such processing aids can include, the non-limiting examples of aromatic, naphthenic and/or paraffinic processing oils, and combinations thereof. In one more specific embodiment, typical amounts of antioxidants are from about 1 to about 5 phr. In one other specific embodiment, representative antioxidants include, the non-limiting examples of diphenyl-p-phenylenediamine and others, e.g., those disclosed in the Vanderbilt Rubber Handbook (1978), pages 344-346. In yet another embodiment, typical amounts of antiozonants, are from about 1 to about 5 phr. In one more embodiment, typical amounts of fatty acids, if used, which can include the non-limiting example of stearic acid, are from about 0.5 to about 3 phr. In one more embodiment, typical amounts of zinc oxide are from about 2 to about 5 phr. In yet another specific embodiment, typical amounts of waxes are from about 1 to about 5 phr. In one embodiment, often microcrystalline waxes are used. In another embodiment, typical amounts of peptizers are from about 0.1 to about 1 phr. In yet a further embodiment, typical peptizers include, the non-limiting examples of pentachlorothiophenol, dibenzamidodiphenyl disulfide and combinations thereof.

In one embodiment herein, rubber compositions herein can be used for various purposes. In one specific embodiment, for example, they can be used for the non-limiting examples of various tire compounds, shoe soles, hoses, cable jackets, gaskets, and other industrial goods. In a more specific embodiment, such articles can be built, shaped, molded and cured by various known and conventional methods as is readily apparent to those skilled in the art. In one even more specific embodiment, one particularly useful application of the rubber compositions herein is for the manufacture of tire treads. In one embodiment, an advantage of tires, tire treads, or other articles of manufacture derived from the rubber compositions herein is that they suffer from less VOC emissions during their lifetime and use as a result of having been manufactured from a rubber compound that contains less residual silane ethoxy groups than do rubber compounds of the known and currently practiced art. In a more specific embodiment, this is a direct result of having used dialkoxy-functional silane coupling agents in their manufacture, which contain fewer or essentially no ethoxy groups on silicon, relative to the blends of alkylsilane and mercaptosilane coupling agents of the currently known and practiced art. In one embodiment, the lack or reduction of ethoxysilane groups in the coupling agents used results in fewer residual ethoxy groups on silicon after the article of manufacture is produced, from which less or no ethanol can be released by hydrolysis of the residual ethoxysilane groups by exposure of the article of manufacture to water during use.

All references cited herein are incorporated by reference herein in their entirety.

The invention can be better understood by reference to the following examples in which the parts and percentages are by weight unless otherwise indicated.

EXAMPLES

Comparative Example 1

Into a 200 ml glass jar were charged n-octyltriethoxysilane (66.5 grams, 0.241 mole) and 3-mercaptopropyltriethoxysilane (15.5 grams, 0.065 mol). The jar was purged with dry nitrogen, sealed and then shaken for 1 minute to thoroughly mix the two components. The n-octyltriethoxysilane and 3-mercaptopropyltriethoxysilane were obtained from GE Advanced Materials—Silicones under the trade names SILQUEST® A-137 silane and SILQUEST® A-1891 silane, respectively.

Comparative Example 2

Into a 100 ml glass jar were charged polyalkyleneoxidealkoxysilane, obtained from GE Advanced Materials—Silicones under the trade names SILQUEST® A-1230 silane (48.7 grams) and 3-mercaptopropyltriethoxysilane (8.2 grams, 0.034 mol). The jar was purged with dry nitrogen, sealed and then shaken for 1 minute to thoroughly mix the two components. The polyalkyleneoxidealkoxysilane and 3-mercaptopropyltriethoxysilane were obtained from GE Advanced Materials—Silicones under the trade names SILQUEST® A-1230 silane and SILQUEST® A-1891 silane, respectively.

Example 3 n-Octyltriethoxysilane (219 grams, 0.792 mole) and 3-mercaptopropyltriethoxysilane (81 grams, 0.34 mole) were added to a 500 ml round-bottomed flask equipped with a magnetic stirrer, short path condenser and receiver flask. Sulfuric acid (0.3 g) was added to the reaction flask and the mixture was heated to 50° C. under a vacuum of 50 torr. 2-Methylpropane-1,3-diol (306 grams, 3.395 moles) was added via addition funnel. Ethanol (155 grams, 3.37 moles) was collected. A 21% ethanolic solution of sodium ethoxide (1.45 g) was added to neutralize the catalyst.

Example 4

3-Mercaptopropyltriethoxysilane (272 grams, 1.143 moles) was added to a 500 ml round-bottomed flask equipped with a magnetic stirrer, short path condenser and receiver flask. Sulfuric acid (0.19 g) was added to the reaction flask and the mixture was heated to 50° C. under a vacuum of 50 torr. 2-Methylpropane-1,3-diol (308 grams, 3.42 moles) was added via addition funnel. Ethanol (152 g) was collected. A 21% ethanolic solution of sodium ethoxide (0.72 g) was added to neutralize the catalyst.

Example 5

Polyalkyleneoxidealkoxysilane, obtained from GE Advanced Materials—Silicones under the trade names SILQUEST® A-1230 silane, (557 grams) was added to a round-bottomed flask equipped with a magnetic stirrer, short path condenser and receiver flask. Sulfuric acid (0.41 g) was added to the reaction flask and the mixture was heated to 50° C. under a vacuum of 50 torr. 2-Methylpropane-1,3-diol (287 grams, 3.18 moles) was added via addition funnel. Methanol (58 grams, 1.8 moles) was collected. A 21% ethanolic solution of sodium ethoxide (1.35 g) was added to neutralize the catalyst.

Example 6

Into a 100 ml glass jar were charged the silane from Example 4 (62.9 grams) and silane from Example 5 (19.7 grams). The jar was purged with dry nitrogen, sealed and then shaken for 1 minute to thoroughly mix the two components.

Example 7

Polyalkyleneoxidealkoxysilane, obtained from GE Advanced Materials—Silicones under the trade names SILQUEST® A-1230 silane, (746 grams) and 3-mercaptopropyltrimethoxysilane (157 grams, 0.80 moles) were added to a round-bottomed flask equipped with a magnetic stirrer, short path condenser and receiver flask. Sulfuric acid (0.76 g) was added to the reaction flask and the mixture was heated to 50° C. under a vacuum of 50 torr. 2-Methylpropane-1,3-diol (594 grams, 6.59 moles) was added via addition funnel. Methanol (157 grams) was collected. A 21% ethanolic solution of sodium ethoxide (1.45 g) was added to neutralize the catalyst.

Comparative Examples 8 and 9

Examples 10 and 11

Cured rubber compositions in the form of plaques (Comparative Examples 8 and 9 employing the silanes of Comparative Examples 1 and 2, respectively, and Examples 10 and 11 employing the silanes of Examples 3 and 6, respectively) were prepared and their physical and dynamic properties measured.

A typical silica-rubber SBR formulation was used as described below in Table 1. Mixing was carried out in a 1550 ml Krupp intermeshing mixer. The silane loadings were 8.2 phr.

TABLE 1

Silica-Silane/Rubber Formulation

| PHR | Components |
|---|---|
| 103.2 | sSBR (Buna VSL 5525-1) - (Bayer AG) |
| 25 | BR (Budene 1207) - (Goodyear) |
| 80 | silica - Zeosil 1165MP, (Rhodia) |
| 8.2 | Silane |
| 4.5 | oil - Sundex 8125 (Sun Oil) |
| 2.5 | zinc oxide - Kadox 720C (ZincCorp.) |
| 1.0 | stearic acid - Industrene R (Witco, Crompton) |
| 2.0 | 6 PPD - Flexzone 7P (Uniroyal, Crompton) |
| 1.5 | Wax - Sunproof Improved (Uniroyal, Crompton) |
| | Final Mix Ingredients |
| 1.4 | Rubbermakers Sulfur 104, Harwick |
| 1.7 | CBS - Delac S (Uniroyal, Crompton) |
| 2.0 | DPG - (Uniroyal, Crompton) |

The procedure which was used for preparing a single non-productive mix is presented in Table 2 below.

TABLE 2

One Pass Procedure; Cooling with water @ 25° C., 68% fill factor:

| Step | Procedure |
|---|---|
| 1 | Add polymers, RDM (ram down mix) 60 seconds |
| 2 | Add 50% silica, all silane, oil, RDM 60 seconds |
| 3 | Add remaining 50% silica, wax, RDM 90 seconds |

TABLE 2-continued

One Pass Procedure; Cooling with water @ 25° C., 68% fill factor:

| Step | Procedure |
|---|---|
| 4 | Dust down, RDM 30 seconds |
| 5 | Add remainder of ingredients, RDM 60 seconds |
| 6 | Dust down, RDM to 160-170° C. (in approx. 2 minutes) by increasing rotor speed |
| 7 | Hold at 170° C. (or higher temperature) for 8 minutes by changing speeds on the mixer. |
| 8 | Dump, sheet off roll mill @ 65-70° C. to cool |

The procedure for preparing a single productive mix involved adding sulfur and accelerators (primary and secondary) into a masterbatch prepared as described in Table 2 on a two-roll mill at 65 to 70° C. After all the silica filler, silane and oil were incorporated into a given mix, the rpm of the rotors was raised so as to achieve the desired silanization temperature. The mix was then held at that temperature for 8 minutes. The mix procedures are shown in Table 2, above.

Curing and testing of the cured rubber compositions in the form of plaques were carried out according to ASTM standards. In addition, small strain dynamic tests were carried out on a Rheometrics Dynamic Analyzer (ARES—Rheometrics Inc.). The specific curing procedure, measurements and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical Properties:

Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$, tan $\delta_{max}$ were extracted from the non-linear responses of the rubber compounds at small strains. In some cases, steady state values of tan $\delta$ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz. The rheological, physical and dynamic properties of the rubber compounds, Comparative Examples 8 and 9 and Example 10 and 11 are given in Table 3.

TABLE 3

The rheological, physical and dynamic properties of filled elastomers made with silanes herein.

| Example Number | 8 | 9 | 10 | 11 |
|---|---|---|---|---|
| Mooney Viscosity @ 100° C. | | | | |
| ML1 + 4 | 61 | 100.97 | 55.86 | 70.39 |
| Mooney Scorch @ 135° C. | | | | |
| $M_v$ | 32.12 | 54.05 | 28.07 | 34.21 |
| MS1+, $t_3$, minutes | 9.01 | 9.01 | 9.29 | 7.44 |
| MS1+, $t_{18}$, minutes | 12.54 | 11.02 | 11.37 | 10.58 |

TABLE 3-continued

The rheological, physical and dynamic properties of filled elastomers made with silanes herein.

| Example Number | 8 | 9 | 10 | 11 |
|---|---|---|---|---|
| Oscillating Disc Rheometer @ 149° C., 1° arc, 30 minute timer | | | | |
| $M_L$, dNm | 8.19 | 14.69 | 7.51 | 10.20 |
| $M_H$, dNm | 28.3 | 40.35 | 28.54 | 32.05 |
| $M_H$-$M_L$ | 20.11 | 25.66 | 21.03 | 21.85 |
| $t_{s1}$, minutes | 5.43 | 2.68 | 5.67 | 4.35 |
| t90, minutes | 21.89 | 16.12 | 9.86 | 10.91 |
| Physical Properties, cured t90 @ 149° C. | | | | |
| Hardness, Shore A | 47.3 | 56.7 | 52 | 54.0 |
| Elongation, % | 428 | 379 | 416 | 432 |
| 25% Modulus, MPa | 0.64 | 0.89 | 0.77 | 0.82 |
| 100% Modulus, MPa | 1.58 | 2.2 | 2.04 | 1.9 |
| 300% Modulus, MPa | 10.23 | 14.6 | 12.74 | 12.7 |
| Tensile, MPa | 18.78 | 20.8 | 20.55 | 22.4 |
| RI 300/25 | 16.01 | 16.43 | 16.50 | 15.42 |
| RI 300/100 | 6.49 | 6.55 | 6.26 | 6.58 |
| DIN Abrasion mm³ loss | 96 | | 122 | |
| Dynamic Properties in the Cured State Non-linearity (0-10%) @ 60° C. | | | | |
| $G'_{initial}$ (MPa) | 2.39 | | 1.89 | |
| ΔG' (MPa) | 1.17 | | 0.75 | |
| $G''_{max}$ (MPa) | 0.28 | | 0.19 | |
| $tan\delta_{max}$ | 0.14 | | 0.12 | |
| Low Temperature Viscoelasticity | | | | |
| tan δ 0° C. | 0.34 | | 0.42 | |
| tan δ 60° C. | 0.13 | | 0.12 | |

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A mercaptofunctional silane composition comprising at least one organofunctional silane selected from the group consisting of:
   (i) mercaptosilane possessing at least one hydroxyalkoxysilyl group and/or a cyclic dialkoxysilyl group,
   (ii) hydrocarbylsilane or heterocarbylsilane possessing at least one hydroxyalkoxysilyl group and/or a cyclic dialkoxysilyl group,
   (iii) mercaptosilane dimer in which the silicon atoms of the mercaptosilane units are bonded to each other through a bridging dialkoxy group, each silane unit optionally possessing at least one hydroxyalkoxysilyl group and/or a cyclic dialkoxysilyl group,
   (iv) hydrocarbylsilane and/or heterocarbylsilane dimer in which the silicon atoms of the hydrocarbylsilane and/or heterocarbylsilane units are bonded to each other through a bridging dialkoxy group, each silane unit optionally possessing at least one hydroxyalkoxysilyl group and/or a cyclic dialkoxysilyl group,
   (v) silane dimer possessing a mercaptosilane unit, the silicon atom of which is bonded to the silicon atom of a hydrocarbylsilane or heterocarbylsilane unit through a bridging dialkoxy group, each silane unit optionally possessing at least one hydroxyalkoxysilyl group and/or a cyclic dialkoxysilyl group,
   (vi) mercaptosilane oligomer in which the silicon atoms of adjacent mercaptosilane units are bonded to each other through a bridging dialkoxy group, the terminal mercaptosilane units possessing at least one hydroxyalkoxysilyl group and/or a cyclic dialkoxysilyl group,
   (vii) hydrocarbylsilane and/or heterocarbylsilane oligomer in which the silicon atoms of adjacent hydrocarbylsilane or heterocarbylsilane units are bonded to each other through a bridging dialkoxy group, the terminal hydrocarbylsilane and/or heterocarbylsilane units possessing at least one hydroxyalkoxysilyl group and/or a cyclic dialkoxysilyl group, and
   (viii) silane oligomer possessing at least one mercaptosilane unit and at least one hydrocarbylsilane or heterocarbylsilane unit, the silicon atoms of adjacent silane units being bonded to each other through a bridging dialkoxy group, the terminal silane units possessing at least one hydroxyalkoxysilyl group and/or a cyclic dialkoxysilyl group, with the provisos that,
   where the composition contains one or more of (i), (iii) and (vi), the composition additionally contains one or more of (ii), (iv), (v), (vii) and (viii), and where the composition contains one or more of (ii), (iv) and (vii), the composition additionally contains one or more of (i), (iii), (v), (vi) and (viii).

2. The mercaptofunctional silane composition of claim 1 comprising at least one mixture selected from the group consisting of (i) and one or more of (ii), (iv), (v), (vii) and (viii); (ii) and one or more of (iii), (v), (vi) and (viii); (iii) and one or more of (v), (vii) and (viii); (iv) and one or more of (v), (vi) and (viii); (v) and either or both of (vi) and (vii); (vi) and either or both of (vii) and (viii); and, (vii) and (viii).

3. The mercaptofunctional silane composition of claim 1 wherein (i) possesses one or two hydroxyalkoxysilyl groups and/or a cyclic dialkoxysilyl group; (ii) possesses one or two hydroxyalkoxysilyl groups and/or a cyclic dialkoxysilyl group; each silane unit of (iii) independently possesses one or two hydroxyalkoxysilyl groups and/or a cyclic dialkoxysilyl group; each silane unit of (iv) independently possesses one or two hydroxyalkoxysilyl groups and/or a cyclic dialkoxysilyl group; each silane unit of (v) independently possesses one or two hydroxyalkoxysilyl groups and/or a cyclic dialkoxysilyl group; (vi) possesses from 3 to about 20 mercaptosilane units, the terminal mercaptosilane units independently possessing one or two hydroxyalkoxysilyl groups and/or a cyclic dialkoxysilyl group; (vii) possesses from 3 to about 20 hydrocarbylsilane and/or heterocarbylsilane units, the terminal hydrocarbylsilane or heterocarbylsilane units independently possessing one or two hydroxyalkoxysilyl groups and/or a cyclic dialkoxysilyl group; and, (viii) possesses from 3 to about 40 silane units of which from 1 to about 20 are mercaptosilane units and from 1 to about 20 are hydrocarbylsilane and/or heterocarbylsilane units, the terminal silane units independently possessing one or two hydroxyalkoxysilyl groups and/or a cyclic dialkoxysilyl group.

4. The mercaptofunctional silane composition of claim 2 wherein (i) possesses one or two hydroxyalkoxysilyl groups and/or a cyclic dialkoxysilyl group; (ii) possesses one or two hydroxyalkoxysilyl groups and/or a cyclic dialkoxysilyl group; each silane unit of (iii) independently possesses one or two hydroxyalkoxysilyl groups and/or a cyclic dialkoxysilyl group; each silane unit of (iv) independently possesses one or two hydroxyalkoxysilyl groups and/or a cyclic dialkoxysilyl group; each silane unit of (v) independently possesses one or two hydroxyalkoxysilyl groups and/or a cyclic dialkoxysilyl group; (vi) possesses from 3 to about 10 mercaptosilane units, the terminal mercaptosilane units independently possessing one or two hydroxyalkoxysilyl groups and/or a cyclic dialkoxysilyl group; (vii) possesses from 3 to about 10 hydrocarbylsilane and/or heterocarbylsilane units, the terminal hydrocarbylsilane or heterocarbylsilane units independently possessing one or two hydroxyalkoxysilyl groups and/or a cyclic dialkoxysilyl group; and, (viii) possesses from 3 to about 20 silane units of which from 1 to about 10 are mercaptosilane units and from 1 to about 10 are hydrocarbylsilane and/or heterocarbylsilane units, the terminal silane units independently possessing one or two hydroxyalkoxysilyl groups and/or a cyclic dialkoxysilyl group.

5. The mercaptofunctional silane composition of claim 2 wherein in each mixture, the ratio of mercaptan to hydrocarbyl group and/or heterocarbyl group ranges from about 20:1 to about 0.05:1.

6. A mercaptofunctional and cyclic and/or bridging dialkoxy silane composition comprising at least one mercaptofunctional silane having a chemical structure selected from the group consisting of:

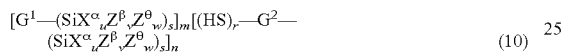

(10)

and

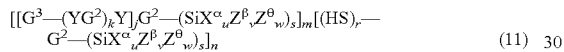

(11)

wherein:
each occurrence of Y is independently selected from a polyvalent species $(-Q)_a[C(=E)]_b(A-)_c$, wherein the atom (E) is attached to an unsaturated carbon atom;

each occurrence of $G^1$ is independently selected from the group consisting of monovalent and polyvalent groups derived by substitution of alkyl, alkenyl, aryl, or aralkyl wherein $G^1$ can have from 1 to about 30 carbon atoms;

each occurrence of $G^2$ is independently selected from the group consisting of divalent or polyvalent group derived by substitution of alkyl, alkenyl, aryl, or aralkyl wherein $G^2$ can have from 1 to 30 carbon atoms;

each occurrence of $G^3$ is independently selected from the group consisting of monovalent and polyvalent groups derived by substitution of alkyl, alkenyl, aryl, or aralkyl wherein $G^3$ can have from 1 to about 30 carbon atoms, with the proviso that if $G^3$ is monovalent, $G^3$ can be hydrogen;

each occurrence of $X^\alpha$ is independently selected from the group consisting of —Cl, —Br, RO—, RC(=O)O—, $R_2C$=NO—, $R_2NO$—, $R_2N$—, —R, $(HO)_{d-1}G^4O$—, $HO(CR^o_2)_fO$—, $HO(CR^o_2CR^o_2O)_e$— wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^4$ is independently a substituted hydrocarbon group from about 2 to about 15 carbon atoms or a substituted heterocarbon groups from about 4 to about 15 carbon atoms and contains one or more etheric oxygen atoms, $R^o$ is independently given by one of the members listed for R, f is 2 to about 15 and e is 2 to about 7;

each occurrence of Q is independently selected from the group consisting of oxygen, sulfur, and (—NR—) and with the proviso that when Q is sulfur, b is 0;

each occurrence of A is independently selected from the group consisting of oxygen, sulfur, and (—NR—) and with the proviso that when A is sulfur, b is 0;

each occurrence of E is independently selected from the group consisting of oxygen, sulfur, and (—NR—);

each occurrence of $Z^\beta$, which forms a bridging structure between two silicon atoms, is independently selected from the group consisting of, $[-OG^4(OH)_{d-2}O-]_{0.5}$, $[-O(CR^o_2CR^o_2O)_e-]_{0.5}$ and $[-O(R^oCR^o)_fO-]_{0.5}$, wherein each occurrence of $R^o$ is independently given by one of the members listed above for R; and each occurrence of $G^4$ is independently selected form the group consisting of a substituted hydrocarbon group from 2 to 15 carbon atoms or a substituted hetercarbon from 4 to 15 carbon atoms and contain one or more etheric oxygen atoms;

each occurrence of $Z^\theta$, which forms a cyclic structure with a silicon atom, is independently given by —$OG^4$ $(OH)_{d-2}O$—, —$O(CR^o_2CR^o_2O)_e$— and —$O(R^oCR^o)_f$ O— wherein each occurrence of $R^o$ is independently given by one of the members listed above for R;

each occurrence of the subscripts, a, b, c, d, e, f, j, k, m, n, r, s, u, v, and w are integers independently given by a is 0 or 1; b is 0 or 1; c is 0 or 1; d is from about 2 to about 8; e is from about 2 to about 7; f is from about 2 to about 15; j is 1 to about 3; k is 0 to about 15; m is from about 1 to about 20; n is from about 1 to about 20; r is from 1 to about 3; and s is from 1 to about 3; u is 0 to 3; v is 0 to 3; w is 0 to about 1 with the proviso that u+v+2w=3; and with the proviso that the each of the above structures (10) and/or (11) contains at least one hydrolysable group, $Z^\beta$ or $Z^\theta$.

7. The mercaptofunctional silane composition of claim 6 wherein Y is selected from the group consisting of —C(=NR)—; —(C=O)—; (—NR)C(=O)—; —OC(=O)—; —OC(=S)—; —OC(=O)O—; —C(=S)—; —C(=O)O—; (—NR)C(=O)(NR—); (—NR)C(=NR)(NR—); —O—; —S—; —SS—; and —NR—.

8. The mercaptofunctional silane composition of claim 7 wherein Y is selected from the group consisting of —O—; —NR—; —C(=O)O—; —C(=O)NR— and (—NR)C (=O)(NR—).

9. The mercaptofunctional silane composition of claim 6 where in Formula (11) Y is —O— or —NR—, $G^2$ is a divalent or polyvalent group derived by substitution of $C_1$-$C_{12}$ alkyl; $G^3$ is hydrogen or $C_1$ to $C_{12}$ straight chain alkyl; $Z^\beta$ is $[-O(R^oCR^o)_fO-]_{0.5}$ and $Z^\theta$ is —$O(R^oCR^o)_f$ O— wherein $R^o$ is hydrogen or methyl and f is 2 or 3, m and n are 1 to about 5, k is 1 to about 5, j is 1 and r is 1 to about 2.

10. The mercaptofunctional silane composition of claim 6 where in Formula (10) $G^1$ is a monovalent straight chain group derived from a $C_3$-$C_{10}$ alkyl, and $G^2$ is a divalent or polyvalent group derived by substitution of a $C_1$-$C_{10}$ alkyl, $Z^\beta$ is $[-O(R^oCR^o)_fO-]_{0.5}$ and $Z^\theta$ is —$O(R^oCR^o)_fO$— wherein $R^o$ is hydrogen or methyl and f is 2 or 3, m and n are 1 to about 5 and r is 1 to about 2.

11. The mercaptofunctional silane composition of claim 6 wherein both the silanes of Formulae (10) and (11) are present.

12. The mercaptofunctional silane composition of claim 6 wherein each $G^1$ is independently $CH_3(CH_2)_g$— and g is from 1 to about 29; benzyl; 2-phenylethyl; cyclohexyl; any of the isomers of —$CH_2CH_2$-norbornane; —$CH_2CH_2$-cyclohexane; branched alkyl groups of from 1 to 30 carbon atoms; or any of the monoradicals obtainable from norbornane, cyclohexane, cyclopentane, tetrahydrodicyclopentadiene, or cyclododecene by loss of one hydrogen atom.

13. The mercaptofunctional silane composition of claim 12 wherein branched alkyl groups of from 1 to 30 carbon atoms are selected from the group consisting of $CH_3(CH_2)_4CH(CH_2CH_3)CH_2$—, $CH_3CH_2CH(CH_2CH_3)CH_2$—, $CH_3CH(CH_3)CH_2$—, $CH_3CH_2CH(CH_3)CH_2$—, and $CH_3(CH_2)_4CH(CH_3)CH_2$—.

14. The mercaptofunctional silane composition of claim 6 wherein each $G^2$ is independently selected from the group consisting of diethylene cyclohexane; 1,2,4-triethylene cyclohexane; phenylene; any of the structures derivable from divinylbenzene; any of the structures derivable from dipropenylbenzene; any of the structures derivable from piperylene; any of the isomers of —$CH_2CH_2$-norbornyl-; any of the diradicals obtainable from tetrahydrodicyclopentadiene or cyclododecene by loss of two hydrogen atoms; any of the structures derivable from limonene; any of the monovinyl-containing structures derivable from trivinylcyclohexane; any of the monounsaturated structures derivable from myrcene containing a trisubstituted C=C; and any of the monounsaturated structures derivable from myrcene lacking a trisubstituted C=C; —$(CH_2)_g$— wherein g is preferably an integer of from 1 to 30, which represent terminal straight-chain alkyls further substituted terminally at the other end, and their beta-substituted analogs; methyl substituted alkylene groups; any structure derivable from methallyl chloride; any of the structures derivable from butadiene; and, any of the diradicals obtainable from norbornane, cyclohexane, or cyclopentane, by loss of two hydrogen atoms.

15. The mercaptofunctional silane composition of claim 6 wherein each $G^3$ is independently hydrogen, $CH_3(CH_2)_g$—, wherein g is 1 to about 29; benzyl; 2-phenylethyl; cyclohexyl; any of the isomers of —$CH_2CH_2$-norborane; any of the isomers of —$CH_2CH_2$-cyclohexane; branched alkyl groups of 1 to 30 carbon atoms; or any of the monoradicals obtainable from norbornane, cyclohexane, cyclopentane, tetrahydrodicyclopentadiene, or cyclododecene by loss of one hydrogen atom.

16. The mercaptofunctional silane composition of claim 6 where in Formulae (10) and/or (11) the sum of the carbon atoms in the hydrocarbonyl and/or heterocarbyl groups for $G^6$, $G^2$ and $G^3$ groups is from about 3 to about 18.

17. The mercaptofunctional silane composition of claim 16 wherein the sum of the carbon atoms in the hydrocarbonyl and/or heterocarbyl groups for $G^1$, $G^2$ and $G^3$ groups is from about 6 to about 14.

18. The mercaptofunctional silane composition of claim 6 wherein $G^1$ is $CH_3CH_2CH_2CH_2CH_2CH_2CH_2$— and $G^2$ is —$CH_2CH_2CH_2$—, r is 1 and s is 1.

19. The mercaptofunctional silane composition of claim 6 wherein the v and w in Formulae (10) and (11) are such that the ratio v/w is between 0 and 1.

20. The mercaptofunctional silane composition of claim 6 wherein, u is from 1 to about 2 with the proviso that u+v+2w=3.

21. The mercaptofunctional silane composition of claim 6 that contains cyclic and/or bridging dialkoxysilyl groups, mercapto groups, and hydrocarbyl and/or heterocarbyl silane is selected from the group consisting of 3-{4-methyl-2-[2-(4-methyl-2-pentyl-[1,3,2]dioxasilolan-2-yloxy)-propoxy]-[1,3,2]dioxasilolan-2-yl}-propane-1-thiol; 3-{2-[2-(2-methyl-[1,3,2]dioxasilolan-2-yloxy)-ethoxy]-[1,3,2]dioxasilolan-2-yl}-propane-1-thiol; mixture of 3-[2-(3-mercapto-propyl)-[1,3,2]dioxasilinan-2-yloxy]-propan-1-ol and 3-(2-butyl-[1,3,2]dioxasilinan-2-yloxy)-propan-1-ol; 4-{2-[3-(2-butyl-[1,3,2]dioxasilinan-2-yloxy)-propoxy]-[1,3,2]dioxasilinan-2-yl}-butane-1-thiol; 4-[2-(3-{2-[3-(2-methoxy-ethoxy)-propyl]-[1,3,2]dioxasilinan-2-yloxy}-propoxy)-[1,3,2]dioxasilinan-2-yl]-butane-1-thiol; 4-[5-methyl-2-(2-methyl-3-{5-methyl-2-[3-(2-methylamino-ethylamino)-propyl]-[1,3,2]dioxasilinan-2-yloxy}-propoxy)-[1,3,2]dioxasilinan-2-yl]-butane-1-thiol; 2-acetylamino-N-[3-(2-{3-[2-(4-mercapto-butyl)-5-methyl-[1,3,2]dioxasilinan-2-yloxy]-2-methyl-propoxy}-5-methyl-[1,3,2]dioxasilinan-2-yl)-propyl]-acetamide; (2-{3-[3-(2-{3-[2-(4-mercapto-butyl)-5-methyl-[1,3,2]dioxasilinan-2-yloxy]-2-methyl-propoxy}-5-methyl-[1,3,2]dioxasilinan-2-yl)-propyl]-ureido}-ethyl)-urea; 4-acetoxy-butyric acid 3-(2-{3-[2-(4-mercapto-butyl)-5,5-dimethyl-[1,3,2]dioxasilinan-2-yloxy]-2,2-dimethyl-propoxy}-5,5-dimethyl-[1,3,2]dioxasilinan-2-yl)-propyl ester; carbonic acid 2-[3-(2-{3-[2-(4-mercapto-butyl)-5,5-dimethyl-[1,3,2]dioxasilinan-2-yloxy]-2,2-dimethyl-propoxy}-5,5-dimethyl-[1,3,2]dioxasilinan-2-yl)-propoxycarbonyloxy]-ethyl ester methyl ester; 4-{[3-(2-dodecyl-4,4,6-trimethyl-[1,3,2]dioxasilinan-2-yloxy)-1,1-dimethyl-butoxy]-dimethyl-silanyl}-butane-1-thiol; 4-{[3-(2-dodecyl-4,4,6-trimethyl-[1,3,2]dioxasilinan-2-yloxy)-1,1-dimethyl-butoxy]-diethoxy-silanyl}-butane-1-thiol; 4-[butyl-[3-(2-dodecyl-4,4,6-trimethyl-[1,3,2]dioxasilinan-2-yloxy)-1,1-dimethyl-butoxy]-(4-mercapto-butyl)-silanyloxy]-2-methyl-pentan-2-ol; 4-{(3-hydroxy-2-methyl-propoxy)-(4-mercapto-butyl)-[2-methyl-3-(5-methyl-2-octyl-[1,3,2]dioxasilinan-2-yloxy)-propoxy]-silanyl}-2-methyl-butan-1-ol; 3-{(3-hydroxy-2-methyl-propoxy)-(4-mercapto-butyl)-[2-methyl-3-(5-methyl-2-octyl-[1,3,2]dioxasilinan-2-yloxy)-propoxy]-silanyloxy}-2-methyl-propan-1-ol; 4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(4-mercapto-butyl)-silanyl]-2-methyl-butan-1-ol; 3-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(4-mercapto-butyl)-silanyloxy]-2-methyl-propan-1-ol; 3-[{3-[(3-hydroxy-2-methyl-propoxy)-{4-[(3-hydroxy-2-methyl-propoxy)-methyl-octyl-silanyloxy]-3-methyl-butyl}-(3-mercapto-propyl)-silanyloxy]-2-methyl-propoxy}-(3-hydroxy-2-methyl-propyl)-octyl-silanyloxy]-2-methyl-propan-1-ol; 4-((3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(3-mercapto-propyl)-silanyl]-2-methyl-butoxy}-octyl-silanyl)-2-methyl-butan-1-ol; 3-((3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-octyl-silanyloxy]-2-methyl-propoxy}-(3-mercapto-propyl)-silanyl]-2-methyl-butoxy}-octyl-silanyl)-2-methyl-propan-1-ol; 4-(benzyl-(3-hydroxy-2-methyl-propoxy)-{4-[(3-hydroxy-2-methyl-propoxy)-{3-[(3-hydroxy-2-methyl-propoxy)-(3-hydroxy-2-methyl-propyl)-phenethyl-silanyloxy]-2-methyl-propoxy}-(3-mercapto-propyl)-silanyl]-2-methyl-butoxy}-silanyl)-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]oxasilolan-2-yloxy)-propoxy]-silanyl}-2-methyl-butoxy)-pent-4-enyl-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]oxasilolan-2-yloxy)-propoxy]-silanyl}-2-methyl-butoxy)-(3-mercapto-propyl)-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-phenethyl-[1,2]

oxasilolan-2-yloxy)-propoxy]-silanyl}-2-methyl-butoxy)-(3-mercapto-propyl)-silanyl]-2-methyl-butan-1-ol; 4-[(3-hydroxy-2-methyl-propoxy)-(4-{(3-hydroxy-2-methyl-propoxy)-(3-mercapto-propyl)-[2-methyl-3-(4-methyl-2-octyl-oxasilolan-2-yloxy)-propoxy]-silanyl}-2-methyl-butoxy)-(3-mercapto-propyl)-silanyl]-2-methyl-butan-1-ol; and combinations thereof.

22. A mercaptofunctional silane composition of claim 1 having a reduced level of VOC.

23. A mercaptofunctional silane composition of claim 6 having a reduced level of VOC.

* * * * *